United States Patent [19]
Williams et al.

[11] Patent Number: 5,968,938
[45] Date of Patent: Oct. 19, 1999

[54] PIPERAZINE OXYTOCIN RECEPTOR ANTAGONISTS

[75] Inventors: Peter D. Williams, Harleysville; Michelle A. Sparks, Gwynedd Valley; Ian Bell, Harleysville; James P. Guare, Jr., Quakertown; Roger M. Freidinger, Lansdale, all of Pa.

[73] Assignee: Merck & Co., Inc., Rahway, N.J.

[21] Appl. No.: 09/086,107

[22] Filed: May 29, 1998

Related U.S. Application Data

[60] Provisional application No. 60/050,132, Jun. 18, 1997.

[51] Int. Cl.$^6$ ...................... A61K 31/495; C07D 401/12; C07D 403/12
[52] U.S. Cl. ...................... 514/252; 514/235.8; 514/253; 514/255; 544/121; 544/357; 544/360; 544/295; 544/366; 544/370; 544/388; 544/391
[58] Field of Search ...................... 544/360, 295, 544/357, 391, 388, 121, 366, 370; 514/252, 255, 235.8, 253

[56] References Cited

U.S. PATENT DOCUMENTS

| | | | |
|---|---|---|---|
| 5,464,788 | 11/1995 | Bock et al. | 514/252 |
| 5,726,172 | 3/1998 | Sparks et al. | 514/230.5 |
| 5,756,504 | 5/1998 | Bock et al. | 514/252 |

OTHER PUBLICATIONS

P.D. Williams et al., "Recent Advances in the Development of Oxytocin Receptor Antagonists" *Current Pharmaceutical Design*, (1996), vol. 2, pp. 41–48.

Evans et al, *J. Med Chem.* 36, pp. 3993–4005, 1993.

*Primary Examiner*—Emily Bernhardt
*Attorney, Agent, or Firm*—Philippe L. Durette; Melvin Winokur

[57] ABSTRACT

This invention relates to certain novel piperazine compounds and derivatives thereof, their synthesis, and their use as oxytocin receptor antagonists. One application of these compounds is in the treatment of preterm labor in mammals, especially humans. The ability of the compounds to relax uterine contractions in mammals also makes them useful for treating dysmenorrhea and stopping labor prior to cesarean delivery.

12 Claims, No Drawings

PIPERAZINE OXYTOCIN RECEPTOR ANTAGONISTS

CROSS-REFERENCE TO RELATED APPLICATIONS

The present invention is related to U.S. provisional application Ser. No. 60/050,132 filed Jun. 18, 1997, the contents of which are hereby incorporated by reference.

STATEMENT REGARDING FEDERALLY-SPONSORED R&D

Not Applicable

REFERENCE TO MICROFICHE APPENDIX

Not Applicable

FIELD OF THE INVENTION

The present invention provides novel compounds, novel compositions, methods of their use and methods of their manufacture; such compounds are generally pharmacologically useful as agents in obstetric and gynecologic therapy in mammals. More specifically, the compounds of the present invention are useful in the treatment of preterm labor, dysmenorrhea and for stopping labor preparatory (i.e., prior) to caesarean delivery.

BACKGROUND OF THE INVENTION

In the field of obstetrics, one of the most important problems is the management of preterm labor. A significant number of the pregnancies progressing past 20 weeks of gestation experience premature labor and delivery, which is a leading cause of neonatal morbidity and mortality. Despite major advances in neonatal care, retention of the fetus in utero is preferred in most instances.

Tocolytic (uterine-relaxing) agents that are currently in use include $\beta_2$-adrenergic agonists, magnesium sulfate and ethanol. Ritodrine, the leading $\beta_2$-adrenergic agonist, causes a number of cardiovascular and metabolic side effects in the mother, including tachycardia, increased renin secretion, hyperglycemia (and reactive hypoglycemia in the infant). Other $\beta_2$-adrenergic agonists, including terbutaline and albuterol have side effects similar to those of ritodrine. Magnesium sulfate at plasma concentrations above the therapeutic range of 4 to 8 mg/dL can cause inhibition of cardiac conduction and neuromuscular transmission, respiratory depression and cardiac arrest, thus making this agent unsuitable when renal function is impaired. Ethanol is as effective as ritodrine in preventing premature labor, but it does not produce a corresponding reduction in the incidence of fetal respiratory distress that administration of ritodrine does.

It has been proposed that an oxytocin antagonist would be the ideal tocolytic agent. In the last few years, evidence has accumulated to strongly suggest that the hormone oxytocin may be a physiological initiator of labor in several mammalian species including humans. Oxytocin is believed to exert this effect in part by directly contracting the uterine myometrium and in part by enhancing the synthesis and release of contractile prostaglandins from the uterine endometrium/decidua. These prostaglandins may, in addition, be important in the cervical ripening process. By these mechanisms, the process of labor (term and preterm) is initiated by a heightened sensitivity of the uterus to oxytocin, resulting in part as a result of a well-documented increase in the number of oxytocin receptors in this tissue. This "up-regulation" of oxytocin receptors and enhanced uterine sensitivity appears to be due to trophic effects of rising plasma levels of estrogen towards term. By blocking oxytocin, one would block both the direct (contractile) and indirect (enhanced prostaglandin synthesis) effects of oxytocin on the uterus. An oxytocin blocker, or antagonist, would likely be more efficacious for treating preterm labor than current regimens. In addition, since oxytocin at term has major effects only on the uterus, such an oxytocin antagonizing compound would be expected to have few, if any, side effects.

The compounds of the present invention are also useful in the treatment of dysmenorrhea. This condition is characterized by cyclic pain associated with menses during ovulatory cycles. The pain is thought to result from uterine contractions and ischemia, probably mediated by the effect of prostaglandins produced in the secretory endometrium. By blocking both the direct and indirect effects of oxytocin on the uterus, an oxytocin antagonist is more efficacious for treating dysmenorrhea than current regimens. An additional use for the present invention is for the stoppage of labor preparatory to cesarean delivery.

It is, therefore, a purpose of this invention to provide substances which more effectively antagonize the function of oxytocin in disease states in animals, preferably mammals, especially in humans. It is another purpose of this invention to provide a method of antagonizing the functions of oxytocin in disease states in mammals. It is also a purpose of this invention to develop a method of preventing or treating the oxytocin-related disorders of preterm labor and dysmenorrhea by antagonizing the binding of oxytocin to its receptor.

It has now been found that compounds of the present invention are antagonists of oxytocin and bind to the oxytocin receptor. When the oxytocin receptor is bound by the compounds of the present invention, oxytocin is antagonized by being blocked from its receptor and thus being unable to exert its biologic or pharmacologic effects. The compounds of the present invention are therefore useful in the treatment and prevention of oxytocin-related disorders of animals, preferably mammals and especially humans. These disorders are primarily preterm labor and dysmenorrhea. The compounds are also useful for stoppage of labor preparatory to cesarean delivery.

SUMMARY OF THE INVENTION

The compounds of the present invention are of the formula

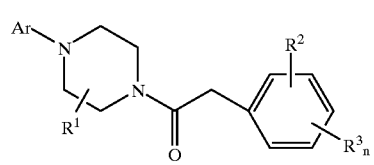

I wherein:
Ar is unsubstituted, mono- or disubstituted phenyl, naphthyl, pyridyl, pyrazinyl or pyrimidinyl, in which the substituents on carbon are independently selected from the group consisting of: $C_{1-5}$ alkyl, $C_{1-5}$ alkoxyl, halogen, nitro, cyano, and $CF_3$;
$R^1$ is H, $CON(R^4)_2$;
$R^2$ is $CF_3$, $OCF_3$, or $OCH_2CF_3$;

$R^3$ is independently selected from the group consisting of: H, halogen, $CF_3$, $OR^5$, $NHR^6$, and Het;

$R^4$ is independently selected from the group consisting of: hydrogen and $C_{1-5}$ alkyl;

$R^5$ and $R^6$ are independently selected from the group consisting of: hydrogen; $C_{1-5}$ alkyl; mono- or polyhalogenated $C_{1-5}$ alkyl; substituted $C_{1-5}$ alkyl wherein the substituent is selected from carboxy, $CO_2$-$C_{1-5}$ alkyl, $CON(R^4)_2$, or morpholinyl; S-$C_{1-5}$ alkyl; SO-$C_{1-5}$ alkyl; $SO_2$-$C_{1-5}$ alkyl; CN; carboxy; CO-$C_{1-5}$ alkyl; $CON(R^4)_2$; pyridinyloxy; pyridinyloxy-N-oxide; triazolyl; tetrazolyl; morpholinyl; unsubstituted or substituted phenoxy wherein the phenoxy is substituted with one to three substituents independently selected from $C_{1-5}$ alkyl, halogen, $CF_3$ or CN;

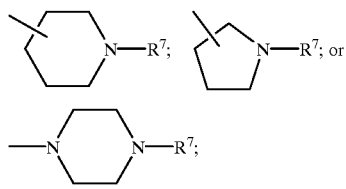

wherein $R^7$ is selected from hydrogen, $C_{1-5}$ alkyl, $C_{3-7}$ cycloalkyl substituted $C_{1-5}$ alkyl, mono or polyhalogenated $C_{1-5}$ alkyl, mono or polyhalogenated $C_{1-5}$ alkyloxycarbonyl, hydroxy $C_{1-5}$ alkyl, $CO_2$-$C_{1-5}$ alkyl, $CON(R^4)_2$, CO-$C_{1-5}$ alkyl, $SO_2$-$C_{1-5}$ alkyl or

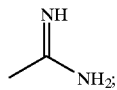

Het is selected from pyridinyl, imidazolyl, triazolyl and morpholinyl; and n is an integer from 1 to 2; and pharmaceutically acceptable salts thereof.

Further embodiments of the invention include compounds of Structure I wherein:

$R^5$ is

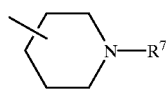

where $R^7$ is selected from the group consisting of: hydrogen, $C_{3-7}$ cycloalkyl substituted $C_{1-5}$ alkyl, $SO_2$-$C_{1-5}$ alkyl, CO-$C_{1-5}$ alkyl, hydroxy $C_{1-5}$ alkyl;

$R^6$ is hydrogen, benzimidazolylcarbonyl, or CO-$C_{1-5}$ alkyl; and

Het is triazolyl; and pharmaceutically acceptable salts thereof.

Still further embodiments include compounds of Structure I wherein

Ar is mono-$C_{1-5}$ alkylsubstituted phenyl;

$R^1$ is $CONH_2$;

$R^2$ is $OCH_2CF_3$; and $R^3$ is

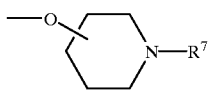

Even further embodiments are compounds of the Structure II:

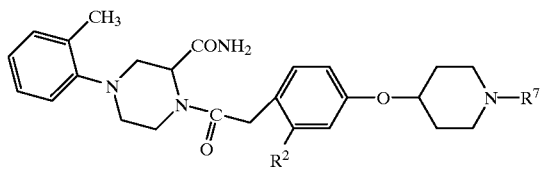

where $R^2$ and $R^7$ are defined above.

Representative compounds of the invention are the following:

1-(4-(4-piperidinyloxy)-2-(2,2,2-trifluoroethoxy) phenylacetyl)-2-carbamoyl-4-(2-methylphenyl) piperazine;

1-(4-(N-cyclopropylmethyl-4-piperidinyloxy)-2-(2,2,2-trifluoroethoxy)phenylacetyl)-2-carbamoyl-4-(2-methylphenyl)piperazine;

1-(4-(N-methylsulfonyl-4-piperidinyloxy)-2-(2,2,2-trifluoroethoxy)phenylacetyl)-2-carbamoyl-4-(2-methylphenyl)piperazine;

1-(4-(N-acetyl-4-piperidinyloxy)-2-(2,2,2-trifluoroethoxy) phenyl-acetyl)-2-carbamoyl-4-(2-methylphenyl) piperazine;

1-(4-(N-2-methyl-2-hydroxypropyl-4-piperidinyloxy)-2-(2,2,2-trifluoroethoxy)phenylacetyl)-2-carbamoyl-4-(2-methylphenyl)-piperazine;

1-(4-amino-2-(2,2,2-trifluoroethoxy)phenylacetyl)-2-carbamoyl-4-(2-methylphenyl)piperazine;

1-(4-(5-benzimidazolylcarbonylamino)-2-(2,2,2-trifluoroethoxy)-phenylacetyl)-2-carbamoyl-4-(2-methylphenyl)piperazine;

1-(2-(2,2,2-trifluoroethoxy)phenylacetyl)-2-carbamoyl-4-(2-methyl-phenyl)piperazine;

1-(2-trifluoromethylphenylacetyl)-2-carbamoyl-4-(2-methylphenyl)-piperazine;

1-(2-trifluoromethoxyphenylacetyl)-2-carbamoyl-4-(2-methylphenyl)-piperazine;

1-(2-(2,2,2-trifluoroethoxy)phenylacetyl)-4-(2-cyanophenyl)piperazine;

1-(2-(2,2,2-trifluoroethoxy)phenylacetyl)-4-(2-methoxyphenyl)-piperazine;

1-(2-(2,2,2-trifluoroethoxy)phenylacetyl)-4-(2-chlorophenyl)piperazine;

1-(2-(2,2,2-trifluoroethoxy)phenylacetyl)-4-(2-pyridyl) piperazine;

1-(4-acetylamino-2-(2,2,2-trifluoroethoxy)phenylacetyl)-2-carbamoyl-4-(2-methylphenyl)piperazine;

1-(4-chloro-2-(2,2,2-trifluoroethoxy)phenylacetyl)-2-carbamoyl-4-(2-methylphenyl)piperazine;

1-(5-chloro-2-(2,2,2-trifluoroethoxy)phenylacetyl)-2-carbamoyl-4-(2-methylphenyl)piperazine;

1-(4-trifluoromethyl-2-(2,2,2-trifluoroethoxy) phenylacetyl)-2-carbamoyl-4-(2-methylphenyl) piperazine;

1-(5-trifluoromethyl-2-(2,2,2-trifluoroethoxy) phenylacetyl)-2-carbamoyl-4-(2-methylphenyl) piperazine;

1-(4-(2-pyridinyloxy)-2-(2,2,2-trifluoroethoxy) phenylacetyl)-2-carbamoyl-4-(2-methylphenyl) piperazine;

1-(3-chloro-2-(2,2,2-trifluoroethoxy)phenylacetyl)-2-carbamoyl-4-(2-methylphenyl)piperazine;

1-(2-(2,2,2-trifluoroethoxy)phenylacetyl)-4-(3-trifluoromethylphenyl)-piperazine;

1-(2-(2,2,2-trifluoroethoxy)phenylacetyl)-4-(2-pyrazinyl) piperazine 1-(2-(2,2,2-trifluoroethoxy)phenylacetyl)-4-(2-pyrimidinyl) piperazine 1-(2-(2,2,2-trifluoroethoxy)phenylacetyl)-4-(2,6-dimethylphenyl)-piperazine 1-(4-(1-triazolyl)-2-(2,2,2-trifluoroethoxy)phenylacetyl)-2-carbamoyl-4-(2-methylphenyl)piperazine;

1-(2-(2,2,2-trifluoroethoxy)phenylacetyl)-4-(4-fluorophenyl)piperazine 1-(4-fluoro-2-(2,2,2-trifluoroethoxy)phenylacetyl)-2-carbamoyl-4-(2-methylphenyl)piperazine;

1-(2-(2,2,2-trifluoroethoxy)phenylacetyl)-4-(2-naphthyl) piperazine 1-(2-(2,2,2-trifluoroethoxy)phenylacetyl)-2-N-methylcarbamoyl-4-(2-methylphenyl)piperazine;

1-(2-(2,2,2-trifluoroethoxy)phenylacetyl)-2-N-ethylcarbamoyl-4-(2-methylphenyl)piperazine;

1-(2-(2,2,2-trifluoroethoxy)phenylacetyl)-2-N,N-dimethylcarbamoyl-4-(2-methylphenyl)piperazine;

1-(4-(4-piperidinyloxy)-2-(trifluoromethoxy)phenylacetyl)-2-carbamoyl-4-(2-methylphenyl)piperazine;

1-(4-(N-acetyl-4-piperidinyloxy)-2-(trifluoromethoxy) phenylacetyl)-2-carbamoyl-4-(2-methylphenyl) piperazine; and 1-(2-(2,2,2-trifluoroethoxy)phenylacetyl)-4-(3-ethylphenyl) piperazine, and pharmaceutically acceptable salts thereof.

A preferred class of compounds of the invention are the following:

1-(4-(4-piperidinyloxy)-2-(2,2,2-trifluoroethoxy) phenylacetyl)-2-carbamoyl-4-(2-methylphenyl) piperazine;

1-(4-(N-cyclopropylmethyl-4-piperidinyloxy)-2-(2,2,2,-trifluoroethoxy)phenylacetyl)-2-carbamoyl-4-(2-methylphenyl)piperazine;

1-(4-(N-methylsulfonyl-4-piperidinyloxy)-2-(2,2,2-trifluoroethoxy)-phenylacetyl)-2-carbamoyl-4-(2-methylphenyl)piperazine;

1-(4-(N-acetyl-4-piperidinyloxy)-2-(2,2,2-trifluoroethoxy) phenyl-acetyl)-2-carbamoyl-4-(2-methylphenyl) piperazine;

1-(4-(N-2-methyl-2-hydroxypropyl-4-piperidinyloxy)-2-(2, 2,2-trifluoroethoxy)phenylacetly)-2-carbamoyl-4-(2-methylphenyl)-piperazine.

1-(4-acetylamino-2-(2,2,2-trifluoroethoxy)phenylacetyl)-2-carbamoyl-4-(2-methylphenyl)piperazine;

1-(4-(1-triazolyl)-2-(2,2,2-trifluoroethoxy)phenylacetyl)-2-carbamoyl-4-(2-methylphenyl)piperazine;

1-(2-(2,2,2,-trifluoroethoxy)phenylacetyl)-4-(2-naphthyl) piperazine;

1-(4-(4-piperidinyloxy)-2-(trifluoromethoxy)phenylacetyl)-2-carbamoyl-4-(2-methylphenyl)piperazine;

1-(4-(N-acetyl-4-piperidinyloxy)-2-(trifluoromethoxy) phenylacetyl)-2-carbamoyl-4-(2-methylphenyl) piperazine; and pharmaceutically acceptable salts thereof.

Illustrating the invention is a pharmaceutical composition comprising any of the compounds described above and a pharmaceutically acceptable carrier. An example of the invention is a pharmaceutical composition made by combining any of the compounds described above and a pharmaceutically acceptable carrier. An illustration of the invention is a process for making a pharmaceutical composition comprising combining any of the compounds described above and a pharmaceutically acceptable carrier.

Further illustrating the invention is a method of eliciting an oxytocin antagonizing effect in a mammal in need thereof, comprising administering to the mammal a therapeutically effective amount of any of the compounds or pharmaceutical compositions described above to elicit an oxytocin antagonizing effect.

An example of the invention are methods of treating preterm labor, preventing preterm labor, stopping preterm labor, stopping labor preparatory to cesarian delivery, and/or treating dysmenorrhea in a mammal in need thereof, comprising administering to the mammal a therapeutically effective amount of any of the compounds or pharmaceutical compositions described above.

Further exemplifying the invention is the use of any of the compounds described above in the preparation of a medicament for the treatment of preterm labor, dysmenorrhea and/or stoppage of labor prior to cesarian delivery in a mammal in need thereof.

More particularly illustrating the invention is a drug which is useful for treating preterm labor, dysmenorrhea and/or stopping labor prior to cesarian delivery in a mammal in need thereof, the effective ingredient of the said drug being any of the compounds descibed above.

More specifically exemplifying the invention are methods of increasing fertility and embryonic survival in a farm animal in need thereof, and/or controlling the timing of estrus in a farm animal in need thereof, comprising administering to the farm animal a therapeutically effective amount of any of the compounds or pharmaceutical compositions described above.

Another example of the invention is a method for improving survival of a farm animal neonate comprising controlling timing of parturition to effect delivery of the neonate during daylight hours by administering to a farm animal which is expected to deliver the neonate within 24 hours a therapeutically effective amount of any of the compounds or pharmaceutical compositions described above.

Additional illustrations of the instant invention are methods of antagonizing vasopressin from binding to its receptor site, inducing vasodilation, treating hypertension, inducing diuresis and/or inhibiting platelet agglutination in a mammal in need thereof comprising the step of administering to the mammal a therapeutically effective amount of any of the compounds or pharmaceutical compositions described above.

BRIEF DESCRIPTION OF THE DRAWINGS

Not Applicable

DETAILED DESCRIPTION OF THE INVENTION

Representative compounds of the present invention are oxytocin antagonists which display submicromolar affinity for the human oxytocin receptor. Compounds of this invention were found to have $IC_{50}$ values for the human oxytocin receptor in the range of 1–500 nM.

The compounds of the present invention are administered in dosages effective to antagonize the oxytocin receptor where such treatment is needed, as in the treatment of preterm labor. For use in medicine, the salts of the compounds of this invention refer to non-toxic "pharmaceutically acceptable salts." Other salts may, however, be useful in the preparation of the compounds according to the invention or of their pharmaceutically acceptable salts. Salts encompassed within the term "pharmaceutically acceptable salts" refer to non-toxic salts of the compounds of this invention which are generally prepared by reacting the free base with a suitable organic or inorganic acid. Representative salts include the following:

Acetate, Benzenesulfonate, Benzoate, Bicarbonate, Bisulfate, Bitartrate, Borate, Bromide, Calcium, Camsylate, Carbonate, Chloride, Clavulanate, Citrate, Dihydrochloride, Edetate, Edisylate, Estolate, Esylate, Fumarate, Gluceptate, Gluconate, Glutamate, Glycollylarsanilate, Hexylresorcinate, Hydrabamine, Hydrobromide, Hydrochloride, Hydroxynaphthoate, Iodide, Isothionate, Lactate, Lactobionate, Laurate, Malate, Maleate, Mandelate, Mesylate, Methylbromide, Methylnitrate, Methylsulfate, Mucate, Napsylate, Nitrate, N-methylglucamine ammonium salt, Oleate, Oxalate, Pamoate (Embonate), Palmitate, Pantothenate, Phosphate/diphosphate, Polygalacturonate, Salicylate, Stearate, Sulfate, Subacetate, Succinate, Tannate, Tartrate, Teoclate, Tosylate, Triethiodide and Valerate. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The compounds of the present invention, may have chiral centers and occur as racemates, racemic mixtures and as individual diastereomers, or enantiomers with all isomeric forms being included in the present invention. Therefore, where a compound is chiral, the separate enantiomers, substantially free of the other, are included within the scope of the invention; further included are all mixtures of the two enantiomers. Also included within the scope of the invention are polymorphs and hydrates of the compounds of the instant invention.

The present invention includes within its scope prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with the compound specifically disclosed or with a compound which is not specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985. Metabolites of these compounds include active species produced upon introduction of compounds of this invention into the biological milieu.

The term "therapeutically effective amount" shall mean that amount of a drug or pharmaceutical agent that will elicit the biological or medical response of a tissue, system, animal or human that is being sought by a researcher or clinician.

The term "alkyl" or "Alk" shall mean straight or branched chain alkanes of one to five total carbon atoms, or any number within this range (i.e., methyl, ethyl, 1-propyl, 2-propyl, n-butyl, sec-butyl, tert-butyl, etc.).

The term "alkoxy," as used herein, refers to straight or branched chain alkoxides of the number of carbon atoms specified (e.g., $C_{1-5}$ alkoxy), or any number within this range (i.e., methoxy, ethoxy, etc.).

The term "halogen" shall include iodine, bromine, chlorine and fluorine.

The terms "mono- or polyhalogenated $C_{1-5}$ alkyl," "mono- or polyhalogenated $C_{1-5}$ alkoxy," "mono- or polyhalogenated $C_{1-5}$ alkenyl," "mono- or polyhalogenated $C_{1-5}$ alkynyl" and "mono- or polyhalogenated $C_{1-5}$ hydroxyalkyl," as used herein, include both straight and branched chain $C_{1-5}$ alkanes, alkoxides, alkenes, alkynes or hydroxyalkanes wherein one or more of the hydrogen atoms on the alkyl, alkoxy, alkenyl, alkynyl or hydroxyalkyl chain is replaced with a halogen atom (e.g., $CF_3$, $OCF_3$, $OCH_2CF_3$).

The term "substituted" shall be deemed to include multiple degrees of substitution by a named substitutent.

Where multiple substituent moieties are disclosed or claimed, the substituted compound can be independently substituted by one or more of the disclosed or claimed substituent moieties, singly or plurally.

The term "preterm labor" shall mean expulsion from the uterus of a viable infant before the normal end of gestation, or more particularly, onset of labor with effacement and dilation of the cervix before the 37th week of gestation. It may or may not be associated with vaginal bleeding or rupture of the membranes.

The term "dysmenorrhea" shall mean painful menstruation.

The term "cesarean delivery" shall mean incision through the abdominal and uterine walls for delivery of a fetus.

As used herein, the term "composition" is intended to encompass a product comprising the specified ingredients in the specified amounts, as well as any product which results, directly or indirectly, from combination of the specified ingredients in the specified amounts.

The ability of the compounds of the present invention to antagonize oxytocin makes these compounds useful as pharmacologic agents for mammals, especially for humans, for the treatment and prevention of disorders wherein oxytocin may be involved. Examples of such disorders include preterm labor and dysmenorrhea. These compounds may also find usefulness for stoppage of labor preparatory to cesarean delivery. Additionally, such compounds are useful in inducing contraception in mammals inasmuch as oxytocin antagonists have now been shown to inhibit the release of oxytocin-stimulated luteinizing hormone (LH) by anterior pituitary cells.

The present invention is also directed to combinations of the compounds of the present invention with one or more agents useful in the treatment of disorders such as preterm labor, dysmenorrhea and stopping labor prior to cesarean delivery. More specifically, the compounds of the instant invention may be effectively administered in combination with effective amounts of other tocolytic agents used in the treatment of preterm labor such as β-adrenergic agonists (e.g., ritodrine, isoproterenol, terbutaline, albuterol), magnesium sulfate, ethanol, other oxytocin antagonists (e.g., atosiban), calcium transport blockers (e.g., nicardipine, nifedipine), prostaglandin synthesis inhibitors (e.g., indomethacin), nitric oxide donors (e.g., nitroglycerine, S-nitroso-N-acetylpenicillamine), phosphodiesterase inhibitors, and progestins (e.g., progesterone). Preferred combinations are simultaneous or alternating treatments of an oxytocin receptor antagonist of the present invention and a second tocolytic agent. In accordance with the method of the present invention, the individual components of the combination can be administered separately at different times during the course of therapy or concurrently in divided or single combination forms. The instant invention is therefore to be understood as embracing all such regimes of simultaneous or alternating treatment and the term "administering" is to be interpreted accordingly. The compounds of the instant invention may also be used in combination with antenatal steroids (e.g., dexamethasone). This particular combination has beneficial effects on the neonate by both decreasing uterine activity to prolong gestation and increasing fetal maturation. It will be understood that the scope of combinations of the compounds of this invention with other agents useful for treating oxytocin related conditions includes in principle any combination with any pharmaceutical composition useful for treating preterm labor, dysmenorrhea or stopping labor prior to cesarean delivery.

The oxytocin antagonist compounds of the present invention are also useful for improving reproductive efficiency in farm animals. In certain farm animals (e.g., sheep, cattle, swine, horses and goats), the beginning of the estrous cycle is typically marked by behavioral estrus when the female animal accepts the male for mating. Ovulation of the ovarian follicle occurs shortly after onset of estrus and cells in the follicle give rise to the corpus luteum. The cells that form the corpus luteum produce progesterone and they also produce oxytocin. The secretion of oxytocin from the corpus luteum and/or pituitary acts on the uterine endometrium to stimulate the secretion of prostaglandins (in particular PGF) which, in turn, causes the regression of the corpus luteum of the ovary. PGF is, therefore, the luteolytic hormone. In the cycling animal (i.e., where mating and fertilization have not occurred), destruction of the corpus luteum removes the source of progesterone which is key to the preparation of the uterus for pregnancy. The presence of a viable conceptus (i.e., the embryo and its associated membranes) is necessary to prevent the luteolytic process. In fact, the first key signal that the conceptus must produce is the one to prevent regression of the corpus luteum (i.e., the maternal recognition of pregnancy signal). Thus, in the animal where mating and fertilization have occurred, the conceptus secretes a factor that antagonizes the action of oxytocin to induce luteolysis. This results in maintenance of a functioning corpus luteum and the continued secretion of progesterone which is obligatory to the initiation of pregnancy.

Administration of an oxytocin antagonist of the present invention at this critical period after fertilization (i.e., just prior to or during the period of maternal recognition of pregnancy) supplements the natural signal from the conceptus (i.e., maternal recognition of pregnancy) to prolong corpus luteal function. The result is to increase pregnancy rates by enhancing the chances of impregnation through a reduction in embryonic loss. Thus, to improve fertility and embryonic survival in a farm animal, a mated animal, for example, a mated ewe, is treated with an oxytocin antagonist compound beginning on between day 10 to day 15 after onset of estrus. The oxytocin antagonist compound is administered to the mated animal for a period of one day to three weeks, preferably one week to three weeks, most preferably one week to two weeks.

The compounds of the present invention are also useful for controlling the timing of parturition in farm animals so that delivery of the neonates occurs during the daytime. Approximately 80% of livestock are delivered at night and up to 5 to 10% of newborns die because the deliveries are not monitored properly. An oxytocin antagonist compound of the present invention administered to the mother on the evening before expected delivery delays parturition so that the delivery occurs during the daylight hours. By delaying the timing of parturition, proper monitoring of the delivery and the neonates is ensured, resulting in increased survival rates of the newborns.

In addition, the oxytocin antagonists of the instant invention can also be used to control the timing of estrus in a cycling farm animal by preventing luteal regression. An oxytocin antagonist compound of the instant invention is administered to a cycling farm animal prior to expected estrus to prevent regression of the corpus luteum. Daily administration of the compound retards estrus until administration of the compound ceases. Preferably, the oxytocin antagonist compound is administered at least 1 day prior to expected estrus. By delaying estrus in a group of farm animals, a farmer can synchronize estrus among the group to provide time and cost savings in farm management.

The compounds of the present invention also bind to the vasopressin receptor and are therefore useful as vasopressin antagonists. Vasopressin antagonists are useful in the treatment or prevention of disease states involving vasopressin disorders; thus, the compounds are useful for inducing vasodilation, treating hypertension, inducing diuresis, inhibiting platelet agglutination and treating congestive heart failure.

The compounds of the present invention can be administered in such oral dosage forms as tablets, capsules (each including timed release and sustained release formulations), pills, powders, granules, elixers, tinctures, suspensions, syrups and emulsions. Likewise, they may also be administered in intravenous (both bolus and infusion), intraperitoneal, subcutaneous or intramuscular form, all using forms well known to those of ordinary skill in the pharmaceutical arts. An effective but non-toxic amount of the compound desired can be employed as a tocolytic agent.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician, veterinarian or clinician can readily determine and prescribe the effective amount of the drug required to prevent, counter or arrest the progress of the condition.

Oral dosages of the present invention, when used for the indicated effects, will range between about 0.0025 to 5.0 gm/day orally. More particularly, when administered orally for the treatment of preterm labor, an effective daily dose will be in the range of 0.005 mg/kg to about 100 mg/kg of body weight, preferably, from 0.01mg/kg to 50 mg/kg, most preferably from 0.1 mg/kg to 50 mg/kg, administered in single or divided dose. For oral administration, the compositions are preferably provided in the form of tablets containing 0.01, 0.05, 0.1, 0.5, 1.0, 2.5, 5.0, 10.0, 15.0, 25.0, 50.0, 100 and 500 milligrams of the active ingredient for the symptomatic adjustment of the dosage to the patient to be treated. A medicament typically contains from about 0.01 mg to about 500 mg of the active ingredient, preferably, from about 1 mg to about 100 mg of active ingredient. Intravenously, the most preferred doses will range from 0.1 to about 10 mg/minute during a constant rate infusion. Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittant throughout the dosage regimen.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, zanthan gum and the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamide-phenol, polyhydroxyethyl-aspartamidephenol, or polyethyleneoxidepolylysine substituted with palmitoyl residues. Furthermore, the compounds of the present invention may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

Abbreviations used in the instant specification, particularly the Schemes and Examples, are as follows:
AIBN=azo bis(isobutyronitrile)
Bn=benzyl
Boc=t-butyloxycarbonyl
BOP=benzotriazol-1-yloxytris(dimethylamino) phosphonium hexafluorophosphate
DCC=1,3-dicyclohexylcarbodiimide
DCM=dichloromethane
DEAD=diethyl azodicarboxylate
DIEA=diisopropylethylamine
DMAP=4-dimethylaminopyridine
DME=dimethoxyethane
DMF=dimethylformamide
DMSO=dimethyl sulfoxide
Et=ethyl
EtOAc=ethyl acetate
EtOH=ethanol
EDC=1-ethyl-3-(3-dimethylaminopropyl)carbodiimide
FAB MS=fast atom bombardment mass spectroscopy
HOAc=acetic acid
HOBT or HBT=1-hydroxybenzotriazole
HPLC=high performance liquid chromatography
IPA=isopropyl acetate
LAH=lithium aluminum hydride
LDA=lithium diisopropylamide
m-CPBA or MCPBA=meta-chloroperoxybenzoic acid
Me=methyl
MeOH=methanol
MOM=methoxymethyl
MTBE=methyl tert-butyl ether
NBS=N-bromosuccinimide
NCS=N-chlorosuccinimide
NMR=nuclear magnetic resonance
Ph=phenyl
PPTS=pyridinium p-toluenesulfonate
t-Bu=tert-butyl
TBAF=tetrabutylammonium fluoride
TEA=triethylamine
Tf=triflate, $SO_2CF_3$
TFA=trifluoroacetic acid
THF=tetrahydrofuran
TLC=thin layer chromatography
TMEDA=N, N, N', N'-tetramethylethylenediamine
TMS=trimethylsilyl
TMS-allyl=allyltrimethylsilane The compounds of the present invention can be prepared readily according to the following Flowsheet diagrams and specific examples, or modifications thereof, using readily available starting materials, reagents and conventional synthesis procedures. In these reactions, it is also possible to make use of variants which are themselves known to those of ordinary skill in this art, but are not mentioned in greater detail.

The general procedure for making the compounds claimed in this invention can be readily understood and appreciated by one skilled in the art from viewing the following Flowsheet schemes.

Flowsheet 1 illustrates the basic condensation reaction from which all of the claimed compounds can be prepared. As shown, Structure A can be reacted with Structure B in the presence of a suitable solvent and reagent combination to effect the condensation reaction to form the Structure I, which is the generic description of the claimed compounds in this invention.

The variables Ar, $R^1$, $R^2$, $R^3_n$ are as defined in the Summary of the Invention, and claim 1. In light of these examples, other conventional procedures will become obvious to one skilled in the art for carrying out the condensation to make the novel compounds of Structure I.

FLOWSHEET 1

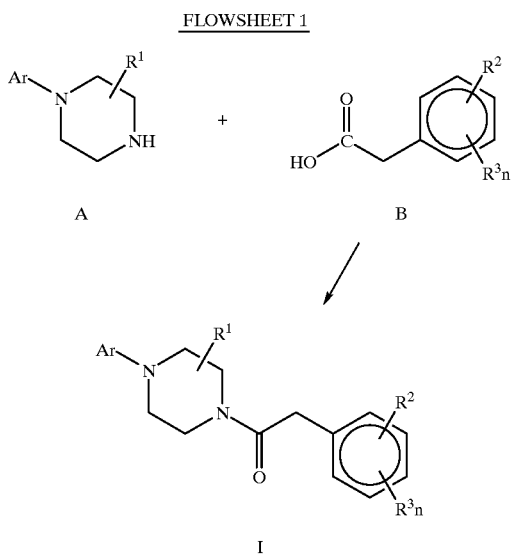

Flowsheet 2 describes three different methods for the synthesis of A. First, an aniline 1 can be reacted with a chloroethylbenzylamine 2 in e.g., toluene with heating to yield an aromatic diamine 3, which can be subsequently reacted with a dibromosubstituted ethyl compound 4 in the presence of $iPr_2NEt$ in DMF with heating, followed by debenzylation to produce the starting generic Structure A. Secondly, the aniline 1 can be reacted with the dichloro substituted amine 6 to produce A. Thirdly, the haloaromatic, where Hal is halogen, can be reacted with the substituted piperazine 8 to produce the aromatic substituted piperazine 9 which can then be deprotected by hydrolysis to yield A.

Flowsheet 3 describes subgeneric Structures $A_1$ and $B_1$ and the synthesis of subgeneric Structure II.

As illustrated, the aniline 10, can be condensed with the N-benzyl-N-chloroethylamine 2 in toluene with heating to produce the aromatic diamine 11. The aromatic diamine 11 can then be reacted with $R^1$ substituted dibromoethylene 12 to produce the ring formed piperazine 13, which can be debenzylated with hydrogen gas over palladium catalyst in methanol to yield the starting intermediate "$A_1$".

The starting intermediate "$B_1$" can be made by reacting the acylphenol 14 with the hydroxypiperidine 15 in THF with triphenylphosphine and DEAD to yield the condensed ether 16. This compound can be converted to the benzylic acid "$B_1$" by treating with thallium nitrate and trimethoxymethane followed by aqueous methanolic sodium hydroxide. "$A_1$" can then be reacted with "$B_1$" in the presence of EDC, HOBT, DIEA and DMF to yield subgeneric Structure II.

FLOWSHEET 3

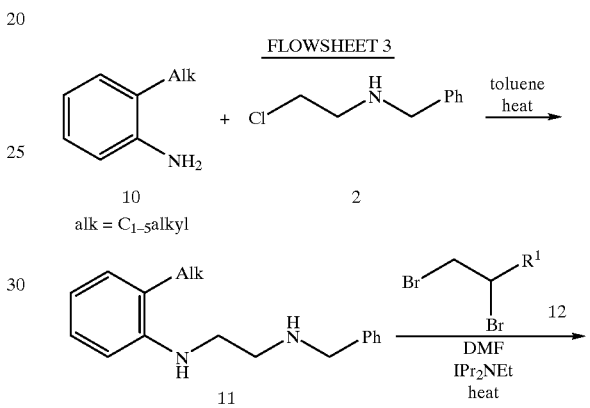

alk = $C_{1-5}$alkyl

FLOWSHEET 2

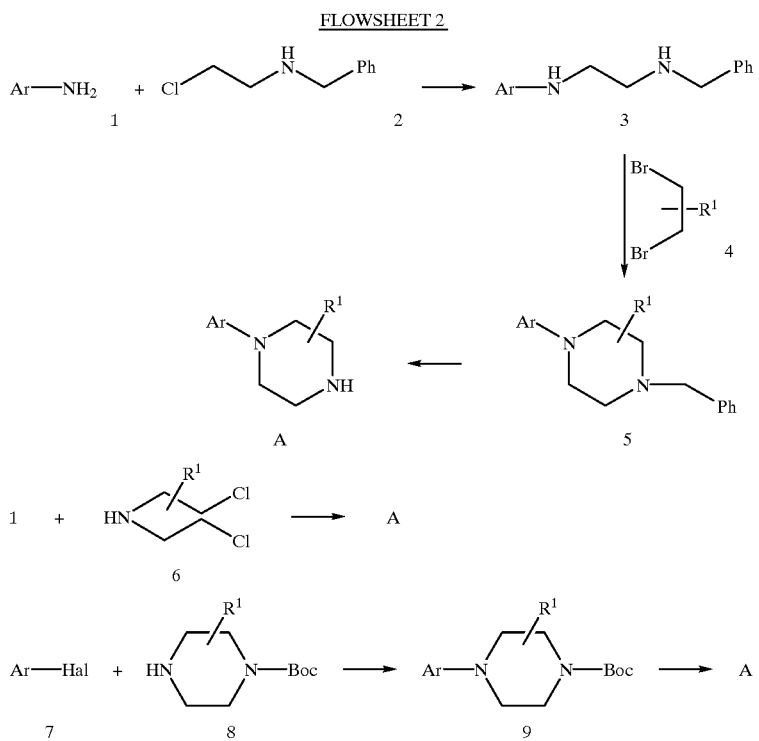

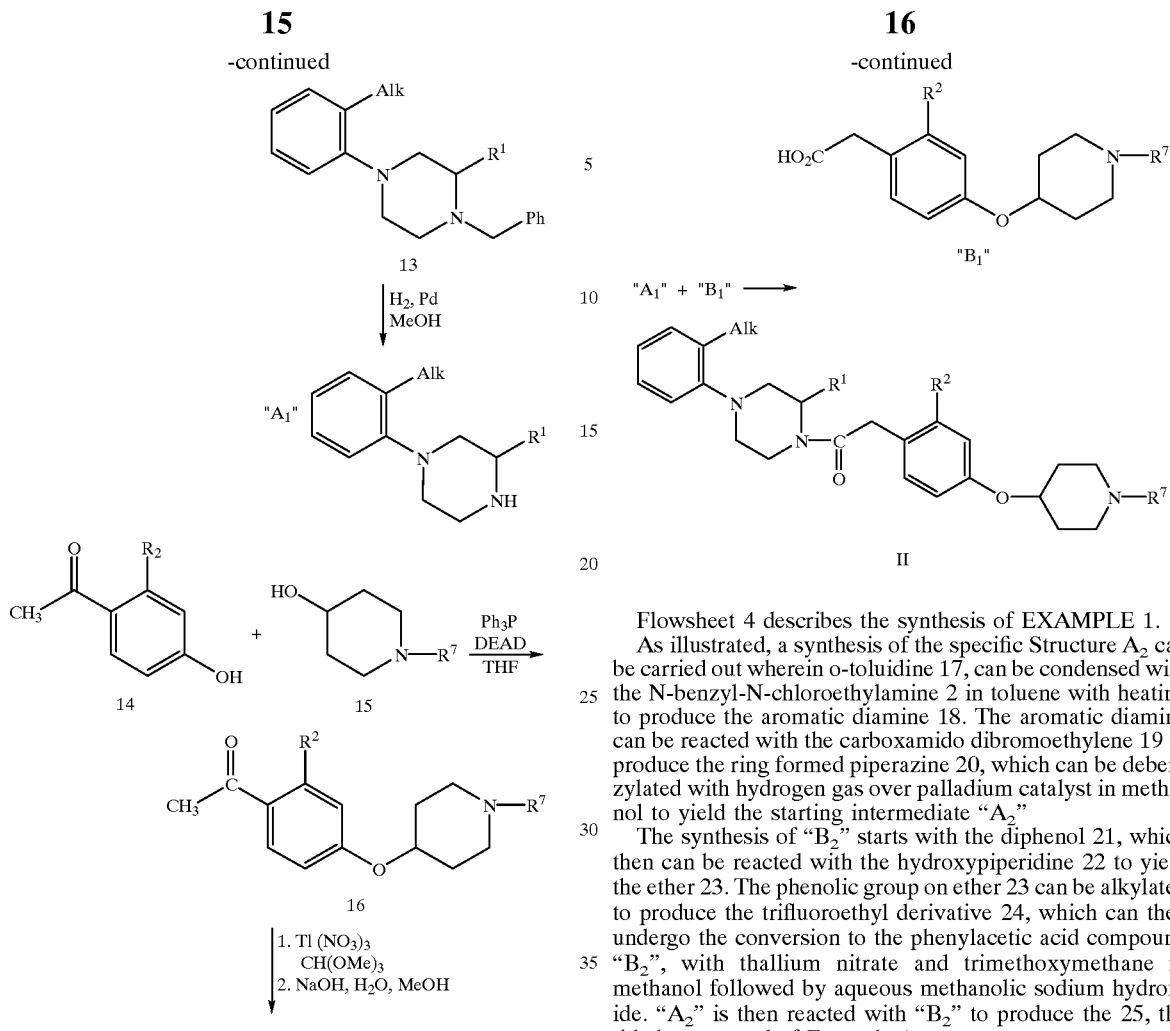

Flowsheet 4 describes the synthesis of EXAMPLE 1.

As illustrated, a synthesis of the specific Structure $A_2$ can be carried out wherein o-toluidine 17, can be condensed with the N-benzyl-N-chloroethylamine 2 in toluene with heating to produce the aromatic diamine 18. The aromatic diamine can be reacted with the carboxamido dibromoethylene 19 to produce the ring formed piperazine 20, which can be debenzylated with hydrogen gas over palladium catalyst in methanol to yield the starting intermediate "$A_2$"

The synthesis of "$B_2$" starts with the diphenol 21, which then can be reacted with the hydroxypiperidine 22 to yield the ether 23. The phenolic group on ether 23 can be alkylated to produce the trifluoroethyl derivative 24, which can then undergo the conversion to the phenylacetic acid compound "$B_2$", with thallium nitrate and trimethoxymethane in methanol followed by aqueous methanolic sodium hydroxide. "$A_2$" is then reacted with "$B_2$" to produce the 25, the titled compound of Example 1.

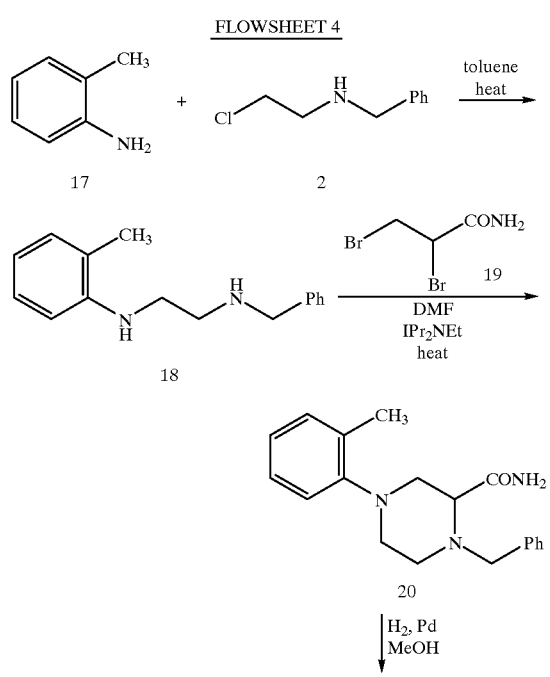

-continued

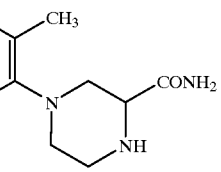

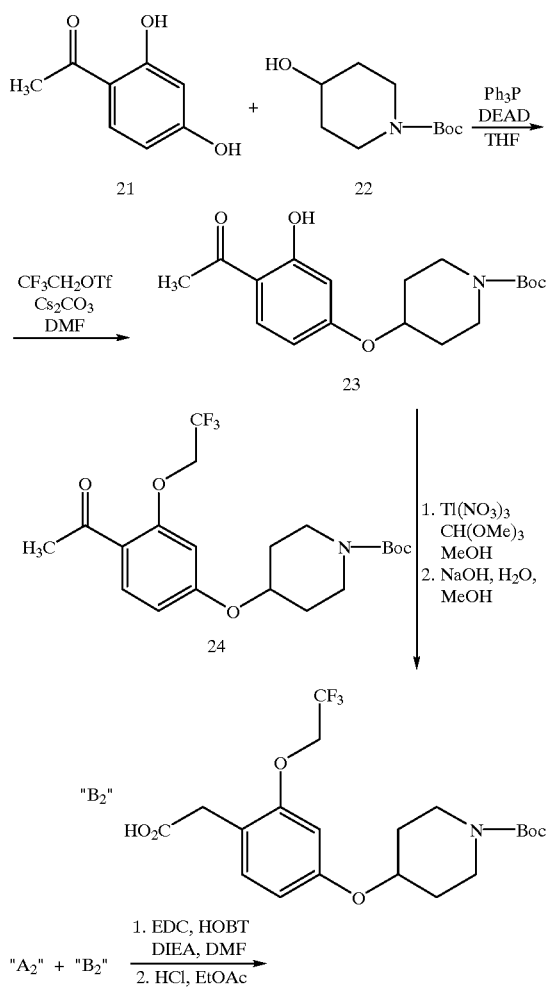

Example 1

Representative compounds of the invention are any or all of those specifically set forth in the following Examples. These compounds are not, however, to be construed as forming the only genus that is considered as the invention, and any combination of the compounds or their moieties may itself form a genus. The following examples further illustrate details for the preparation of the compounds of the present invention. Those skilled in the art will readily understand that known variations of the conditions and processes of the following preparative procedures can be used to prepare these compounds.

In the Examples, dry THF was obtained by distillation from calcium hydride under inert atmosphere. Dry DMF and dry CH$_2$Cl$_2$ were obtained by storing the reagent grade solvents over 3 Å molecular sieves. Determination of reaction pH was estimated by spotting an aliquot from the reaction mixture on wetted E. Merck "colorpHast" pH 1–14 indicator strips. Silica coated TLC plates were used to monitor all reactions (Analtech Uniplate, 2.4×10 cm, Silica Gel GF, 250 micron thickness). Pressurized silica gel column chromatography using 230–400 mesh silica gel was performed according to the method of Still, Kahn, and Mitra, *J. Org. Chem.*, 1978, vol. 43, p. 2923. All temperatures are degrees Celsius. $^1$H NMR spectra were measured at 300 MHz on a Varian XL-300, at 400 MHz on a Varian XL-400, using $(CH_3)_4Si$ as an internal standard. All NMR spectra for the compounds of the Examples which follow were consistent with the assigned structures. Fast atom bombardment mass spectra were obtained on a VG-ZAB-HF spectrometer.

MeOH($NH_3$) used for TLC analysis and for silica gel coulmn chromatography refers to a methanol solution saturated with ammonia gas at 0° C. 2,2,2-Trifluoroethyl trifluoromethylsulfonate and 2,2,3,3,3-pentafluoropropyl trifluoromethylsulfonate were prepared by the method of R. L. Hansen, *J. Orge. Chem.*, 1965, vol. 30, pp.4322–4.

Analytical HPLC were run on a Spectra Physics SP4270/8800 instrument using the following conditions:

Column: Vydac $C_{18}$, 0.21×15 cm

UV detection at 214 nm

Mobile Phase for Methods A–C:

A=0.1% by volume TFA in $H_2O$

B=0.1% by volume TFA in acetonitrile

Mobile Phase for Method D:

A=0.1% by volume $H_3PO_4$ in $H_2O$

B=0.1% by volume $H_3PO_4$ in acetonitrile

Method A:

Gradient T=0 min, 95% A, 5% B

T=15 min, 0% A, 100% B

Flow=2.0 mL/min

Method B:

Gradient T=0 min, 95% A, 5% B

T=15 min, 5% A, 95% B

Flow=1.5 mL/min

Method C:

Gradient T=0 min, 95% A, 5% B

T=45 min, 5% A, 95% B

Flow=1.5 mL/min

Method D:

Gradient T=0 min, 95% A, 5% B

T=15 min, 5% A, 95% B

Flow=1.5 mL/min

EXAMPLE 1

1-(4-(4-piperidinyloxy)-2-(2,2,2-trifluoroethoxy)phenylacetyl)-2-carbamoyl-4-(2-methylphenyl)piperazine

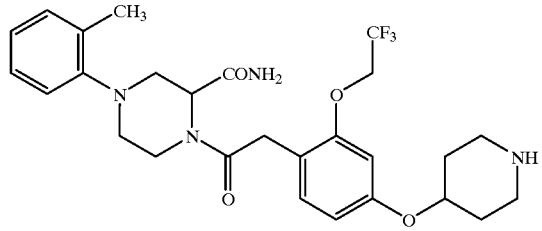

Steps 1–4. 2-Benzylaminoethanol (20 g, 0.13 mol) was converted to N-(2-chloroethyl)-N-benzylamine hydrochloride with thionyl chloride (31 g, 0.26 mol) according to the procedure described in *J. Chem. Soc.* 1955, p. 896. N-(2-chloroethyl)-N-benzylamine hydrochloride (4.0 g, 19 mmol) was converted to N-benzyl-N'-(2-methylphenyl)-1,2-diaminoethane hydrochloride by the procedure of Syn. Comm., 1988, vol. 18, p. 45–50, using o-toluidine (6.1 g, 57 mmol) in place of aniline. 1-Benzyl-2-carbamoyl-4-(2-methylphenyl)-piperazine was prepared from 2,3-dibromopropionamide (7.9 g, 34 mmol) by the procedure of *J. Med. Chem.*, 1992, vol. 35, p. 743–750 using N-benzyl-N'-(2-methylphenyl)- 1,2-diaminoethane hydrochloride (4.95 g, 18 mmol) in place of N-benzyl-N'-phenyl-1,2-diaminoethane hydrochloride (TLC: Rf=0.51 (5% methanol in methylene chloride; FABMS: M+H @ m/e=310). 1-Benzyl-2-carbamoyl-4-(2-methyl-phenyl)piperazine (2.64 g, 8.53 mmol) and palladium hydroxide/carbon (430 mg) were combined in a mixture of methanol (35 ml) and ethanol (35 ml) and shaken in an atmosphere of hydrogen at 55 psi for 6 hours at ambient temperature. The mixture was filtered and the filtrate was concentrated in vacuo. The residue was reconcentrated in vacuo from ether three times to provide 2-carbamoyl-4-(2-methylphenyl)piperazine as a solid.

Step 5. To a stirred solution of 2,4-dihydroxyacetophenone (6.0 g, 39.5 mmol) and triphenylphosphine (15.5 g, 59.2 mmol) in dry THF (100 mL) at 0° C. was added a solution of N-tert-butyloxycarbonyl-4-piperidinol (11.9 g, 59.2 mmol) and DEAD (10.3 g, 59.2 mmol) in dry THF (75 mL) dropwise over a period of 2 h. The mixture was warmed to ambient temperature over 2 h and stirred for an additional 18 h. The solvent was removed under reduced pressure and the residue was suspended in ether. The solid triphenylphosphine oxide was removed by filtration and the filtrate was concentrated under reduced pressure and purified by pressurized silica gel column chromatography using 4:1 hexane:EtOAc as eluant. Concentration of the product-containing fractions gave 4-(N-tert-butyloxycarbonyl-4-piperidinyloxy)-2-hydroxyacetophenone as a solid (HPLC retention time=6.15 min (method A); TLC R$_f$=0.49 (1:3 EtOAc:hexanes)).

Step 6. To a stirred solution of 4-(N-tert-butyloxycarbonyl-4-piperidinyloxy)-2-hydroxyacetophenone (4.0 g, MW=335, 11.9 mmol) from Step 5 above and 2,2,2-trifluoroethyl trifluoromethyl-sulfonate (5.4 g, 26 mmol) in DMF (50 mL) at 0° C. was added $Cs_2CO_3$ (8.5 g, 26 mmol). The mixture was stirred at 0° C. for 2 h and then at ambient temperature for 2 h. The solvent was removed under reduced pressure and the residue was partitioned between EtOAc (150 mL) and saturated aqueous $NaHCO_3$ (200 mL). The organic phase was dried (MgSO$_4$), filtered, and the solvent was removed under reduced pressure. The residue was purified by pressurized silica gel column chromatography using 4:1 hexanes:EtOAc as eluant. The product-containing fractions were evaporated under reduced pressure to give 4-(N-tert-butyloxycarbonyl-4-piperidinyloxy)-2-(2,2,2-trifluoroethoxy)-acetophenone as a colorless gum (HPLC retention time=10.6 min (method A); TLC R$_f$32 0.45 (1:3 EtOAc:hexanes)).

Step 7. To a stirred solution of 4-(N-tert-butyloxy-carbonyl-4-piperidinyloxy)-2-(2,2,2-trifluoroethoxy) acetophenone (4.0 g, 9.88 mmol) from Step 6 above and trimethyl orthoformate (3.15 g, 29.7 mmol) in MeOH (100 mL) was added thallium trinitrate trihydrate (4.39 g, 9.88 mmol). The mixture was stirred at ambient temperature for 18 h. A white solid precipitate was removed by filtration and the filtrate solvent was evaporated under reduced pressure. The residue was partitioned between EtOAc (100 mL) and saturated aqueous NaHCO$_3$ (200 mL). The organic phase was dried (MgSO$_4$), filtered, and the solvent was removed under reduced pressure. HPLC analysis (method A) of the residue indicated a ca. 4:1 mixture of desired product (retention time=10.8 min) and product in which the Boc group had been lost (retention time 6.5 min). The residue was dissolved in DMF (20 mL) and di-tert-butyl dicarbonate (0.72 g, 3.3 mmol) was added. The mixture was stirred at ambient temperature for 2 h. The solvent was removed under reduced pressure and the residue was partitioned between EtOAc (100 mL) and saturated aqueous NaHCO$_3$ (50 mL). The organic phase was dried (MgSO$_4$), filtered, and the solvent was removed under reduced pressure. The residue was purified by pressurized silica gel column chromatography using 4:1 hexanes:EtOAc as eluant. The product-containing fractions were evaporated under reduced pressure to give methyl 4-(N-tert-butyloxycarbonyl-4-piperidinyloxy)-2-(2,2,2-trifluoroethoxy)phenylacetate as a colorless gum (HPLC retention time=10.8 min (method A); TLC R$_f$=0.46 (1:3 EtOAc:hexanes)).

Step 8. To a stirred solution of methyl 4-(N-tert-butyloxy-carbonyl-4-piperidinyloxy)-2-(2,2,2-trifluoroethoxy) phenylacetate (3.0 g, MW=435, 6.90 mmol) from Step 7 above in MeOH (25 mL) was added a solution of aqueous NaOH (6.9 mL of a 2.0 N solution, 13.8 mmol). The mixture was refluxed for 3 h and then cooled to ambient temperature. The solvents were removed under reduced pressure and the residue was partitioned between EtOAc (100 mL) and 0.25 M aqueous citric acid (75 mL). The organic phase was separated and washed with H$_2$O (25 mL) and brine (25 mL). The organic phase was dried (MgSO$_4$), filtered, and the solvent was removed under reduced pressure. 4-(N-tert-butyloxycarbonyl-4-piperidinyloxy)-2-(2,2,2-trifluoroethoxy)phenylacetic acid was obtained as an amorphous solid (HPLC retention time=9.4 min (method A)).

Step 9. To a stirred solution of 4-(N-tert-butyloxy-carbonyl-4-piperidinyloxy)-2-(2,2,2-trifluoroethoxy) phenylacetic acid (2.0 g, MW=421, 4.75 mmol) from Step 8 above, 2-carbamoyl-4-(2-methylphenyl)piperazine (0.89 g, 4.8 mmol) from Step 4 above, and HOBT (0.73g, 4.8 mmol) in DMF (75 mL) was added EDC (2.08 g, 7.1 mmol) and DIEA (1.2 mL, 7.2 mmol). The mixture was stirred at ambient temperature for 14 h. The solvent was removed under reduced pressure and the residue was partitioned between EtOAc (100 mL) and 0.25 M aqueous citric acid (75 mL). The organic phase was separated and washed with H$_2$O (25 mL), saturated aqueous NaHCO$_3$ (75 mL), and brine (25 mL). The organic phase was dried (MgSO$_4$), filtered, and the solvent was removed under reduced pressure. The residue was purified by pressurized silica gel column chromatography using EtOAc as eluant. The product-containing fractions were evaporated under reduced pressure to give 1-(4-(N-Boc-4-piperidinyloxy)-2-(2,2,2-trifluoroethoxy)phenylacetyl)-2-carbamoyl-4-(2-methylphenyl)-piperazine as an amorphous solid.

Step 10. Into a stirred solution of 1-(4-(N-Boc-4-piperidinyloxy)-2-(2,2,2-trifluoroethoxy)phenylacetyl)-2-carbamoyl-4-(2-methylphenyl)piperazine (3.5 g, 5.4 mmol) from Step 9 above in EtOAc (125 mL) at 0° C. was bubbled HCl gas for 15 min. The resulting suspension was stirred at 0° C. for 45 min. Excess HCl was removed by bubbling argon though the mixture for 15 min. Ether (125 mL) was added and the cold suspension was filtered. The solids were washed with additional ether and then dried under reduced pressure for 18 h to give the hydrochloride salt of the title compound as an amorphous white powder.

HPLC retention time=7.35 min (method A) TLC R$_f$=0.22 (90:10:0.5 CH$_2$Cl$_2$:MeOH:NH$_4$OH); FAB MS: m/z=535 (M$^+$+H); combustion analysis: C$_{27}$H$_{33}$F$_3$N$_4$O$_4$, 1.5 HCl, 1.0 H$_2$O; Calculated C, 53.40; H, 6.06; N, 9.23; Found C, 53.56; H, 6.15; N, 9.21

EXAMPLE 2

1-(4-(N-cyclopropylmethyl-4-piperidinyloxy)-2-(2,2,2-trifluoro-ethoxy)phenylacetyl)-2-carbamoyl-4-(2-methylphenylpiperazine

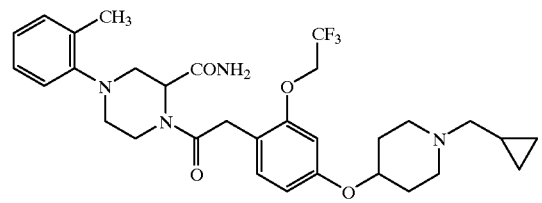

To a solution of 1-(4-(4-piperidinyloxy)-2-(2,2,2-trifluoroethoxy)phenylacetyl)-2-carbamoyl-4-(2-methylphenyl)piperazine hydrochloride (0.30 g, 0.5 mmol) from Example 1 in MeOH (7.5 mL) was added sodium acetate (82 mg, 1.0 mmol), acetic acid (0.10 mL, 1.7 mmol), and cyclopropane carboxaldehyde (75 mg, 1.1 mmol). The mixture was stirred at ambient temperature for 30 min and NaBH$_3$CN (61 mg, 1.0 mmol) was added. The solution was stirred for 18 h and the solvent was removed under reduced pressure. The residue was dissolved in EtOAc (50 mL) and washed with saturated aqueous NaHCO$_3$ (3×25 mL). The organic phase was dried (MgSO$_4$), filtered, and the solvent was removed under reduced pressure. The residue was purified by pressurized silica gel column chromatography using 95:5:0.25 CH$_2$Cl$_2$:MeOH:NH$_4$OH as eluant. The free base was dissolved in MeOH containing 2.5 equivalents of 3 N aqueous HCl. The resulting solution was evaporated under reduced pressure and the residue was dissolved in a minimum volume of MeOH and added dropwise to rapidly stirred ether. The precipitate was collected by filtration and dried in vacuo to give the hydrochloride salt of the title compound as an amorphous solid.

HPLC retention time=9.76 min (method B) TLC R$_f$=0.28 (95:5:0.5 CH$_2$Cl$_2$:MeOH:NH$_4$OH); FAB MS: m/z=589 (M$^+$+H); combustion analysis: C$_{31}$H$_{39}$F$_3$N$_4$O$_4$, 2.15 HCl, 0.15 ether; Calculated C, 55.97; H, 6.34; N, 8.26; Found C, 55.98; H, 6.54; N, 8.36

EXAMPLE 3

1-(4-(N-methylsulfonyl-4-piperidinyloxy)-2-(2,2,2-trifluoroethoxy)-phenylacetyl)-2-carbamoyl-4-(2-methylphenyl)piperazine

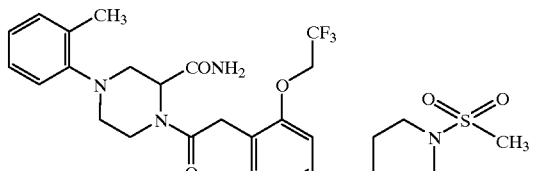

To a solution of 1-(4-(4-piperidinyloxy)-2-(2,2,2-trifluoroethoxy)phenylacetyl)-2-carbamoyl-4-(2-methylphenyl)piperazine hydrochloride (0.20 g, 0.35 mmol) from Example 1 in $CH_2Cl_2$ (20 mL) was added methanesulfonyl chloride (0.045 g, 0.39 mmol) and DIEA (0.14 mL, 0.80 mmol). The solution was stirred at ambient temperature for 6 h and the solvent was removed under reduced pressure. The residue was dissolved in EtOAc (50 mL) and washed with 0.25 M aqueous citric acid (25 mL), $H_2O$ (25 mL), and saturated aqueous $NaHCO_3$ (25 mL). The organic phase was dried ($MgSO_4$), filtered, and the solvent was removed under reduced pressure. The residue was purified by pressurized silica gel column chromatography using 97:3 $CH_2Cl_2$:MeOH. The product-containing fractions were combined and the solvent was removed under reduced pressure. The residue was dissolved in $CH_2Cl_2$:hexane, and evaporation of this solution under reduced pressure gave the title compound as an amorphous solid.

HPLC retention time=11.2 min (method B) TLC $R_f$=0.25 (95:5 $CH_2Cl2$:MeOH); FAB MS: m/z=613 $(M^++H)$, 0.25 $CH_2Cl_2$, 0.35 hexane; combustion analysis: $C_{28}H_{35}F_3N_4O_6S$, 0.25 $CH_2Cl_2$, 0.35 hexane; Calculated C, 64.89; H, 6.13; N, 8.44; Found C, 54.97; H, 6.17; N, 8.43

EXAMPLE 4

1-(4-(N-acetyl-4-piperidinyloxy)-2-(2,2,2-trifluoroethoxy)phenyl-acetyl)-2-carbamoyl-4-(2-methylphenyl)piperazine

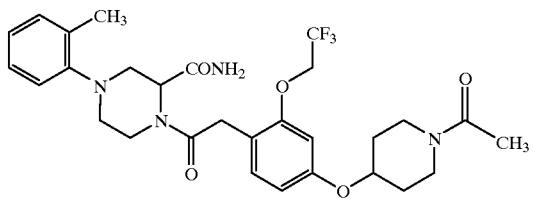

To a solution of 1-(4-(4-piperidinyloxy)-2-(2,2,2-trifluoroethoxy)phenylacetyl)-2-carbamoyl-4-(2-methylphenyl)piperazine hydrochloride (0.30 g, 0.5 mmol) from Example 1 in $CH_2Cl_2$ (50 mL) was added acetic anhydride (0.11 mL, 1.0 mmol) and DIEA (0.17 mL, 1.0 mmol). The solution was stirred at ambient temperature for 1 h and the solvent was removed under reduced pressure. The residue was dissolved in EtOAc (100 mL) and washed with 0.25 M aqueous citric acid (50 mL), $H_2O$ (25 mL), and saturated aqueous $NaHCO_3$ (75 mL). The organic phase was dried ($MgSO_4$), filtered, and the solvent was removed under reduced pressure. The residue was dissolved in $CH_2Cl_2$ and 2 equivalents of TFA were added. Evaporation of this solution under reduced pressure gave the TFA salt of title compound as an amorphous solid.

HPLC retention time=9.29 min (method B) TLC $R_f$=0.15 (95:5:0.5 $CH_2Cl_2$:MeOH:$NH_4OH$); FAB MS: m/z=577 $(M^++H)$, 1.0 TFA, 0.7 $CH_2Cl_2$; combustion analysis: $C_{29}H_{35}F_3N_4O_5$, 1.0 TFA, 0.7 $CH_2Cl_2$; Calculated C, 50.76; H, 5.03; N, 7.47; Found C, 50.77; H, 4.79; N, 7.29

EXAMPLE 5

1-(4-(N-2-methyl-2-hydroxypropyl-4-piperidinyloxy)-2-(2,2,2-trifluoroethoxy) phenylacetyl)-2-carbamoyl-4-(2-methylphenyl)-piperazine

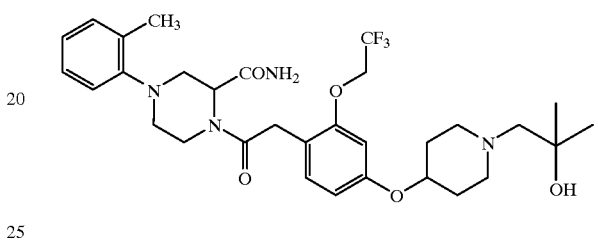

To a solution of 1-(4-(4-piperidinyloxy)-2-(2,2,2-trifluoroethoxy)phenylacetyl)-2-carbamoyl-4-(2-methylphenyl)piperazine hydrochloride (0.10 g, 0.17 mmol) from Example 2 in MeOH (10 mL) was added DIEA (0.035 mL, 0.20 mmol) and isobutylene oxide (1 mL, 13 mmol). The solution was stirred for 18 h at ambient temperature and the solvent was removed under reduced pressure. The residue was dissolved in EtOAc (50 mL) and washed with saturated aqueous $NaHCO_3$ (25 mL). The organic phase was dried ($MgSO_4$), filtered, and the solvent was removed under reduced pressure. The residue was purified by preparative reverse phase HPLC using a water:acetonitrile gradient containing 0.1% TFA. The product-containing fractions were lyophilized to give the TFA salt of the title compound as an amorphous solid.

HPLC retention time=8.40 min (method B) TLC $R_f$=0.26 (92:8:0.8 $CH_2Cl_2$:MeOH:$NH_4OH$); FAB MS: m/z=607 $(M^++H)$; combustion analysis: $C_{31}H_{41}F_3N_4O_5$, 1.8 TFA, 0.1 $H_2O$; Calculated C, 51.07; H, 5.33; N, 6.89; Found C, 51.08; H, 5.25; N, 6.83

EXAMPLE 6

1-(4-amino-2-(2,2,2-trifluoroethoxy)phenylacetyl)-2-carbamoyl-4-(2-methylphenyl)niperazine

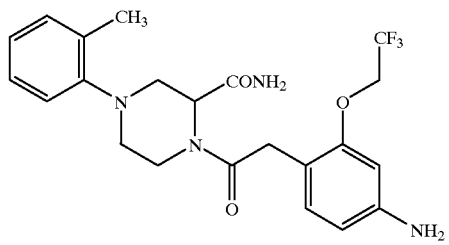

Step 1. To a stirred solution of 4-nitro-2-hydroxytoluene (5 g, 33 mmol) in DMF (75 mL) at 0° C. was added 2,2,2-trifluoroethyl trifluoromethylsulfonate (13 g, 62 mmol) and $Cs_2CO_3$ (20 g, 62 mmol). The mixture was stirred at 0° C. for 30 min and then at ambient temperature for 2 h. The mixture was diluted with EtOAc (150 mL) and filtered. The filtrate solvents were removed under reduced pressure and the residue was dissolved in EtOAc (200 mL) and washed with saturated aqueous $NaHCO_3$ (2×100 mL) and brine (50 mL). The organic phase was dried ($MgSO_4$), filtered, and the volume was reduced to ~50 mL under reduced pressure, at which point the product had begun to crystallize. The mixture was cooled to −20° C. for 14 h, filtered, and the solids were washed with cold EtOAc. 4-Nitro-2-(2,2,2-trifluoroethoxy)toluene was obtained as a crystalline solid (HPLC retention time=10.0 min (method A)).

Step 2. 4-Nitro-2-(2,2,2-trifluoroethoxy)toluene (2.0 g, 9.0 mmol) from Step 1 above was dissolved in MeOH (20 mL) and shaken with palladium black (100 mg) under 50 psig of hydrogen on a Parr apparatus for 2 h. The catalyst was removed by filtration and the solvent was removed under reduced pressure to give 4-amino-2-(2,2,2-trifluoroethoxy)toluene as a gum.

Step 3. To a stirred solution of 4-amino-2-(2,2,2-trifluoroethoxy)toluene (1.2 g, 6.2 mmol) from Step 2 above in DMF (20 mL) was added di-tert-butyldicarbonate (3.4 g, 16 mmol) and DMAP (0.76 g, 6.2 mmol). The mixture was stirred at ambient temperature for 2 h and then at 40° C. for 14 h. The solvent was removed under reduced pressure and the residue was partitioned between EtOAc (100 mL) and 0.25 M aqueous citric acid (75 mL). The organic phase was separated, washed with water (50 mL), saturated aqueous $NaHCO_3$ (50 mL), dried ($MgSO_4$), filtered, and the solvent was removed under reduced pressure. The residue was purified by pressurized silica gel column chromatography using a gradient elution of 5–15% EtOAc:hexanes to give 4-(N,N-di-(tert-butylcarbonyl)amino)-2-(2,2,2-trifluoroethoxy)-toluene as a colorless gum (TLC $R_f$=0.55 (15% EtOAc:hexanes)).

Step 4. To a stirred solution of 4-(N,N-di-(tert-butylcarbonyl)-amino)-2-(2,2,2-trifluoroethoxy)toluene (2.0 g, 5.0 mmol) from Step 3 above in $CCl_4$ (75 mL) was added NBS (0.90 g, 5.0 mmol) and AIBN (0.2 g, 1.2 mmol). The mixture was refluxed for 2 h. The solvent was removed under reduced pressure and the residue was partitioned between EtOAc (100 mL) and saturated aqueous $NaHCO_3$ (2×50 mL). The organic phase was dried ($MgSO_4$), filtered, and the solvent was removed under reduced pressure. The residue was purified by pressurized silica gel column chromatography using a gradient elution of 5–15% EtOAc:hexanes to give 4-(N,N-di-(tert-butylcarbonyl)amino)-2-(2,2,2-trifluoroethoxy)benzyl bromide as a colorless gum (TLC $R_f$=0.50 (15% EtOAc:hexanes)).

Step 5. To a stirred solution of 4-(N,N-di-(tert-butylcarbonyl)-amino)-2-(2,2,2-trifluoroethoxy)benzyl bromide (1.5 g, 3.2 mmol) from Step 4 above in DMF (20 mL) was added NaCN (0.23 g, 4.8 mmol). The mixture was stirred at ambient temperature for 24 h. The solvent was removed under reduced pressure and the residue was purified by pressurized silica gel column chromatography using 15% EtOAc:hexanes as eluant to give an inseparable mixture (~3:1) of 4-(N,N-di-(tert-butylcarbonyl)amino)-2-(2,2,2-trifluoroethoxy)phenyl-acetonitrile and 4-(tert-butylcarbonylamino)-2-(2,2,2-trifluoroethoxy)-phenylacetonitrile (TLC $R_f$=0.28 (15% EtOAc:hexanes)).

Step 6. A ~3:1 mixture of 4-(N,N-di-(tert-butylcarbonyl)-amino)-2-(2,2,2-trifluoroethoxy)phenylacetonitrile and 4-(tert-butylcarbonylamino)-2-(2,2,2-trifluoroethoxy) phenylacetonitrile (1.1 g) from Step 5 above was refluxed in a 1:1 mixture of acetic acid and concentrated aqueous HCl for 3 h. The solvents were removed under reduced pressure. The residue was dissolved in water and the solvent was evaporated under reduced pressure to remove residual acetic acid. 4-Amino-2-(2,2,2-trifluoroethoxy)phenylacetic acid hydrochloride was obtained as a colorless gum (HPLC retention time=4.2 min (method A)).

Step 7. Into a stirred solution of 4-amino-2-(2,2,2-trifluoroethoxy)phenylacetic acid hydrochloride (0.95 g, 3.5 mmol) from Step 6 above in MeOH (25 mL) at 0° C. was bubbled HCl gas for 10 min. The resulting solution was warmed to ambient temperature and stirred for 14 h. The solvent was removed under reduced pressure to give methyl 4-amino-2-(2,2,2-trifluoroethoxy)phenylacetate hydrochloride as a solid (HPLC retention time=5.6 min (method A)).

Step 8. To a solution of methyl 4-amino-2-(2,2,2-trifluoroethoxy)phenylacetate hydrochloride (1.0 g, 3.5 mmol) from Step 7 above in DMF (20 mL) was added di-tert-butyl-dicarbonate (0.85 g, 3.9 mmol) and DIEA (1.2 mL, 7.0 mmol). The solution was stirread at ambient temperature for 14 h. The solvent was removed under reduced pressure and the residue was partitioned between EtOAc (100 mL) and 0.25 M aqueous citric acid (50 mL). The organic phase was separated, washed with water (25 mL), saturated aqueous $NaHCO_3$ (50 mL), dried ($MgSO_4$), filtered, and the solvent was removed under reduced pressure. The residue was purified by pressurized silica gel column chromatography using 20% EtOAc:hexanes as eluant. Methyl 4-(tert-butyloxycarbonylamino)-2-(2,2,2-trifluoroethoxy)phenylacetate was obtained as a colorless gum (TLC $R_f$=0.40 (20% EtOAc:hexanes); HPLC retention time=10.3 min (method A)).

Step 9. To a stirred solution of methyl 4-(tert-butyloxycarbonyl-amino)-2-(2,2,2-trifluoroethoxy) phenylacetate (0.90 g, 2.5 mmol) in MeOH (15 mL) was added aqueous NaOH (2.5 mL of a 3 N solution, 7.5 mmol). The mixture was refluxed for 1 h. The solvents were removed under reduced pressure and the residue was partitioned between EtOAc (100 mL) and 0.25 M aqueous citric acid (25 mL). The organic phase was separated, washed with water (25 mL), dried ($MgSO_4$), filtered, and the solvent was removed under reduced pressure to give 4-(tert-butyloxycarbonylamino)-2-(2,2,2-trifluoroethoxy)-phenylacetic acid as an amorphous solid (HPLC retention time=8.8 min (method A)).

Step 10. To a stirred solution of 4-(tert-butyloxycarbonylmino)-2-(2,2,2-trifluoroethoxy) phenylacetic acid (0.20 g, 0.59 mmol) from Step 9 above in DMF (10 mL) was added 2-carbamoyl-4-(2-methylhenyl) piperazine (0.13 g, 0.59 mmol) from Step 4 of Example 1, HOBT (0.09 g, 0.6 mmol), EDC (0.15 g, 0.90 mmol), and DIEA (0.15 mL, 0.90 mmol). The solution was stirred at ambient temperature for 14 h during which time a precipitate had formed. The mixture was cooled, filtered, and the solid was washed with EtOAc and dried under reduced pressure to give 1-(2-(2,2,2-trifluoroethoxy)-4-(tert-butyloxycarbonylamino)phenylacetyl)-2-carbamoyl-4-(2-methylphenyl)-piperazine as an amorphous solid (HPLC retention time=10.0 min (method A); TLC $R_f$=0.40 (3:1 EtOAc:hexanes).

Step 11. Into a stirred solution of 1-(2-(2,2,2-trifluoroethoxy)-4-(tert-butyloxycarbonylamino) phenylacetyl)-2-carbamoyl-4-(2-methylphenyl)piperazine (0.22 g, 0.41 mmol) from Step 10 above in EtOAc (75 mL) at 0° C. was bubbled HCl gas for 15 min. The resulting suspension was stirred at 0° C. for 45 min. Excess HCl was removed by bubbling argon though the mixture for 15 min. Ether (75 mL) was added and the cold suspension was filtered. The solids were washed with EtOAc and dried under reduced pressure for 18 h to give the hydrochloride salt of the title compound as an amorphous white powder.

HPLC retention time=7.2 min (method A) TLC $R_f$=0.50 (90:10:0.5 $CH_2Cl_2$:MeOH:$NH_4OH$); FAB MS: m/z=451 ($M^+$+H); combustion analysis: $C_{22}H_{25}F_3N_4O_3$, 2.0 HCl, 1.0 $H_{2O}$; $_{0.7}$ EtOAc; Calculated C, 49.07; H, 5.57; N, 9.87; Found C, 49.02; H, 5.49; N, 9.88

EXAMPLE 7

1-(4-(5-benzimidazolylcarbonylamino)-2-(2,2,2-trifluoroethoxy)-phenylacetyl)-2-carbamoyl-4-(2-methylphenyl)piperazine

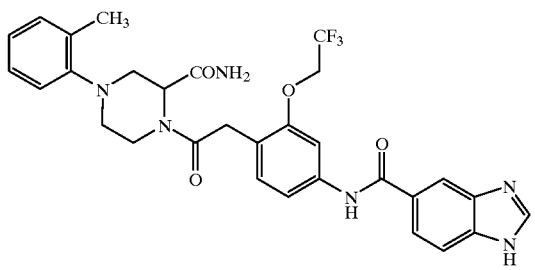

To a stirred solution of 1-(4-amino-2-(2,2,2-trifluoroethoxy)phenylacetyl)-2-carbamoyl-4-(2-methylphenyl)piperazine (0.20 g, 0.44 mmol) from Example 6 in DMF (10 mL) was added benzimidazole 5-carboxylic acid (0.077 g, 0.48 mmol), HOBT (0.09 g, 0.6 mmol), EDC (0.15 g, 0.90 mmol), and DIEA (0.083 mL, 0.5 mmol). The solution was stirred at ambient temperature for 14 h during which time a precipitate had formed. The mixture was cooled, filtered, and the solid was washed with EtOAc. The solid was dissolved in $CH_3CN$:$H_2O$ containing TFA and purified by preparative reverse phase HPLC. The product-containing fractions were lyophilized to give the TFA salt of the title compound as an amorphous solid.

HPLC retention time=8.3 min (method A) TLC $R_f$=0.22 (90:10:0.5 $CH_2Cl_2$:MeOH:$NH_4OH$); FAB MS: m/z=595 ($M^+$+H); combustion analysis: $C_{30}H_{29}F_3N_6O_4$, 2.1 TFA, 2.25 $H_2O$; Calculated C, 46.97; H, 4.10; N, 9.61; Found C, 46.90; H, 3.97; N, 9.61

EXAMPLE 8

1-(2-(2,2,2-trifluoroethoxy)phenylacetyl)-2-carbamoyl-4-(2-methylphenyl)-piperazine

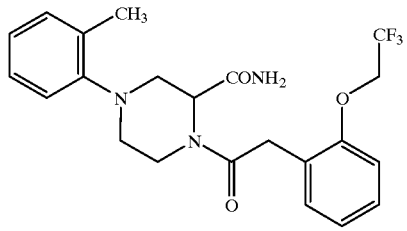

Step 1. To a stirred solution of methyl 2-hydroxyphenylacetate (10 g, 60 mmol) in DMF (150 mL) at 0° C. was added 2,2,2-trifluoroethyl trifluoromethansul- fonate (94 mmol) and $Cs_2CO_3$ (38 g, 120 mmol). The mixture was stirred at 0° C. for 2 h and then at ambient temperature for 12 h. The solids were removed by filtration and the filtrate solvents were removed under reduced pressure. The residue was partitioned between EtOAc (250 mL) and water (2×100 mL). The organic phase was dried ($MgSO_4$), filtered, and the solvent was removed under reduced pressure. The residue was purified by silica gel chromatography to give methyl 2-(2,2,2-trifluoroethoxyphenylacetate as a colorless liquid (HPLC retention time=9.3 min (method E); TLC $R_f$=0.6 (2:1 hexanes:EtOAc)).

Step 2. To a stirred solution of methyl 2-(2,2,2-trifluoroethoxyphenylacetate (2 g, 8 mmol) from Step 1 above in DME (20 mL) was added aqueous LiOH (20 mL of a 1.0 M solution, 20 mmol). The solution was stirred at ambient temperature for 1 h. The solution was concentrated under reduced pressure to ~10 mL and 0.25 M aqueous citric acid (20 mL) was added. The precipitate was removed by filtration and dried under reduced pressure to give 2-(2,2,2-trifluoroethoxyphenylacetic acid as a crystalline solid (HPLC retention time=7.4 min (method E)).

Step 3. To a stirred solution of 2-(2,2,2-trifluoroethoxyphenylacetic acid (0.10 g, 0.45 mmol) from Step 2 above and 2-carbamoyl-4-(2-methylphenyl) piperazine (0.10 g, 0.46 mmol) from Step 4 of Example 1 in DMF (15 mL) was added HOBT (0.075 g, 0.5 mmol), EDC (0.22 g, 0.75 mmol), and DIEA (0.13 mL, 0.75 mmol). The solution was stirred at ambient temperature for 14 h and the solvent was removed under reduced pressure. The residue was partitioned between EtOAc (100 mL) and 0.25 M aqueous citric acid (25 mL). The organic phase was separated and washed with $H_2O$ (25 mL), saturated aqueous $NaHCO_3$ (25 mL), and brine (25 mL). The organic phase was dried ($MgSO_4$), filtered, and the solvent was removed under reduced pressure. The residue was purified by pressurized silica gel coulmn chromatography using 5:95 MeOH:$CH_2Cl_2$ as eluant. The title compound was obtained as an amorphous solid.

HPLC retention time=8.8 min (method A) TLC $R_f$=0.2 (5:95 MeOH:$CH_2Cl_2$); FAB MS: m/z=436 ($M^+$+H); combustion analysis: $C_{22}H_{24}F_3N_3O_3$, 0.15 $CH_2Cl_2$ ; Calculated C, 59.35; H, 5.47; N, 9.38; Found C, 59.41; H, 5.53; N, 9.54

EXAMPLE 9

1-(2-trifluoromethylphenylacetyl)-2-carbamoyl-4-(2-methylphenyl)-

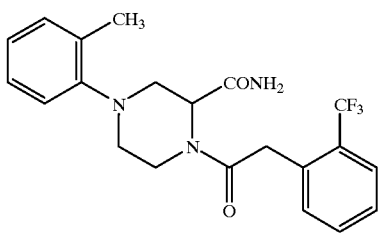

The title compound was prepared from 2-trifluoromethylphenylacetic acid and 2-carbamoyl-4-(2-methylphenyl)piperazine using the procedure given in Step 3 of Example 8. The title compound was obtained as an amorphous solid.

HPLC retention time=8.82 min (method A) TLC $R_f$=0.4 (95:5 $CH_2Cl_2$:MeOH); FAB MS: m/z=406 ($M^+$+H); combustion analysis: $C_{21}H_{22}F_3N_3O_2$, 0.05 $CH_2Cl_2$, 0.05 MeOH; Calculated C, 61.62; H, 5.47; N, 10.22; Found C, 61.57; H, 5.41; N, 10.42

EXAMPLE 10

1-(2-trifluoromethoxyphenylacetyl)-2-carbamoyl-4-(2-methylphenyl)-piperazine

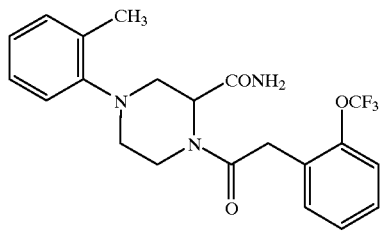

Step 1. To a stirred solution of 2-trifluoromethoxybenzoic acid (1.0 g, 5.2 mmol) in THF (25 mL) at 0° C. was added borane-THF complex (15 mL of a 1.0 M solution in THF, 15 mmol). The solution was warmed to ambient temperature and stirred for 14 h. The solvent was removed under reduced pressure and the residue was partitioned between EtOAc (75 mL) and saturated aqueous $NaHCO_3$ (75 mL). The organic phase was dried ($MgSO_4$), filtered and the solvent was removed under reduced pressure to give 2-trifluoromethoxybenzyl alcohol as a colorless liquid (TLC $R_f$=0.2 (1:3 EtOAc-hexanes)).

Step 2. To a stirred solution of 2-trifluoromethoxybenzyl alcohol (0.81 g, 4.5 mmol) from Step 1 above in ether (20 mL) at 0° C. was added triphenylphosphine (2.4 g, 9.2 mmol) and $CBr_4$ (3.0 g, 9.2 mmol). The mixture was warmed to ambient temperature and stirred for 18 h. The ether was decanted from the gummy precipitate of triphenylphosphine oxide and evaporated under reduced pressure. The residue was purified by pressurized silica gel column chromatography using hexanes as eluant to give 2-trifluoromethoxybenzyl bromide as a colorless liquid (TLC $R_f$=0.80 (hexanes)).

Step 3. To a stirred solution of 2-trifluoromethoxybenzyl bromide (0.95 g, 3.9 mmol) from Step 2 above in DMF (5 mL) was added NaCN (0.21 g, 4.3 mmol). The mixture was stirred at ambient temperature for 14 h and the solvent was removed under reduced pressure. The residue was purified by pressurized silica gel column chromatography using 15% EtOAc-hexanes as eluant to give 2-trifluoromethoxyphenylacetonitrile as a colorless liquid (TLC $R_f$=0.6 (solvent)).

Step 4. 2-Trifluoromethoxyphenylacetonitrile (0.49 g, 2.6 mmol) from Step 3 above was refluxed for 3 h in a 1:1 mixture of acetic acid and concentrated aqueous HCl. The solvents were removed under reduced pressure. The residue was partitioned between EtOAc (75 mL) and water (2×25 mL). The organic phase was separated, dried ($MgSO_4$), filtered, and evaporated under reduced pressure to give 2-trifluoromethoxyphenylacetic acid as an amorphous solid (HPLC retention time=6.8 min (method A)).

Step 5. To a stirred solution of 2-trifluoromethoxyphenylacetic acid (0.10 g, 0.48 mmol) from Step 4 above and 2-carbamoyl-4-(2-methylphenyl) piperazine (0.10 g, 0.46 mmol) from Step 4 of Example 1 in DMF (10 mL) was added HOBT (0.075 g, 0.5 mmol), EDC (0.22 g, 0.75 mmol), and DIEA (0.13 mL, 0.75 mmol). The solution was stirred at ambient temperature for 14 h and the solvent was removed under reduced pressure. The residue was partitioned between EtOAc (50 mL) and 0.25 M aqueous citric acid (25 mL). The organic phase was separated and washed with $H_2O$ (25 mL), saturated aqueous $NaHCO_3$ (25 mL), and brine (25 mL). The organic phase was dried ($MgSO_4$), filtered, and the solvent was removed under reduced pressure. The residue was purified by pressurized silica gel column chromatography using EtOAc as eluant. The product-containing fractions were evaporated under reduced pressure and the residue was lyophilized from $CH_3CN:H_2O$ to give the title compound as an amorphous solid.

HPLC retention time=9.1 min (method A) TLC $R_f$=0.2 (5:95 MeOH:$CH_2Cl_2$); FAB MS: m/z=422 ($M^+$+H); combustion analysis: $C_{21}H_{22}F_3N_3O_3$, 0.3 $H_2O$, 0.1 $CH_3CN$; Calculated C, 59.08; H, 5.36; N, 10.08; Found C, 59.10; H, 5.30; N, 10.17

EXAMPLE 11

1-(2-(2,2,2-trifluoroethoxy)phenylacetyl)-4-(2-cyanophenyl)piperazine

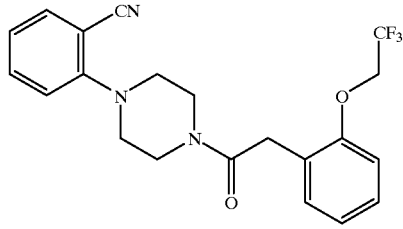

The title compound was prepared using the procedure given in Example 12 using 2-cyanophenylpiperazine in place of 2-methoxyphenylpiperazine. The product was purified by pressurized silica gel column chromatography using 1:1 EtOAc:hexanes as eluant to give the title compound as an amorphous solid.

HPLC retention time=9.7 min (method A) TLC $R_f$=0.5 (1:1 EtOAc:hexanes); FAB MS: m/z=404 ($M^+$+H); combustion analysis: $C_{21}H_{20}F_3N_3O_2$, 0.3 $H_2O$; Calculated C, 61.69; H, 5.08; N, 10.28; Found C, 61.74; H, 4.92; N, 9.98

EXAMPLE 12

1-(2-(2,2,2-trifluoroethoxy)phenylacetyl)-4-(2-methoxyphenyl)-piperazine

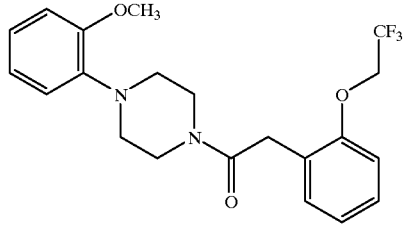

To a stirred solution of 2-methoxyphenylpiperazine (0.062 g, 0.32 mmol) and 2-(2,2,2-trifluoroethoxy) phenylacetic acid (0.075 mg, 0.32 mmol) in DMF (1 mL) was added EDC (0.115 g, 0.40 mmol), HOBT (0.049 g, 0.32 mmol), and DIEA (0.055 mL, 0.32 mmol). The mixture was stirred at ambient temperature for 18 h. The DMF was removed under reduced pressure. The residue was partitioned between EtOAc and saturated aqueous NaHCO₃. The EtOAc layer was dried (MgSO₄), filtered, and the solvent was removed under reduced pressure. The residue was purified by preparative TLC using 1:1 EtOAc:hexane as eluant. The title compound was obtained as an amorphous solid.

HPLC retention time=8.9 min (method D) TLC $R_f$=0.45 (1:1 EtOAc:hexane); FAB MS: m/z=409 (M⁺+H); combustion analysis: $C_{21}H_{23}F_3N_2O_3$; Calculated C, 61.76; H, 5.68; N, 6.86; Found C, 61.65; H, 5.86; N, 6.60

EXAMPLE 13

1-(2-(2,2,2-trifluoroethoxy)phenylacetyl)-4-(2-chlorophenyl)piperazine

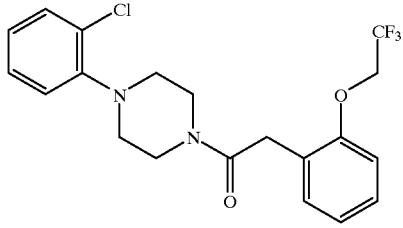

The title compound was prepared and purified using the procedure given in Example 12 using 2-chlorophenylpiperazine in place of 2-methoxyphenylpiperazine.

HPLC retention time=11.5 min (method D) TLC $R_f$=0.57 (1:1 EtOAc:hexanesa); FAB MS: m/z=380 (M⁺+H); combustion analysis: $C_{19}H_{20}F_3N_3O_2$ ; Calculated C, 58.19; H, 4.88; N, 6.78; Found C, 57.72; H, 5.03; N, 6.38

EXAMPLE 14

1-(2-(2,2,2-trifluoroethoxy)phenylacetyl)-4-(2-pyridyl)piperazine

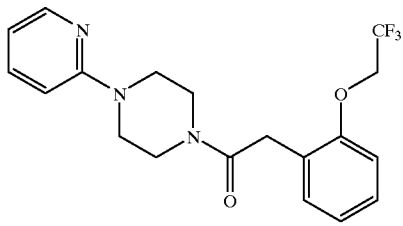

The title compound was prepared and purified using the procedure given in Example 12 using 2-pyridylpiperazine in place of 2-methoxyphenylpiperazine.

HPLC retention time=5.3 min (method D) TLC $R_f$=0.39 (1:1 EtOAc:hexanes); FAB MS: m/z=380 (M⁺+H); combustion analysis: $C_{19}H_{20}F_3N_3O_2$ ; Calculated C, 60.15; H, 5.31; N, 11.08; Found C, 60.25; H, 5.47; N, 10.70

EXAMPLE 15

1-(4-acetylamino-2-(2,2,2-trifluoroethoxy)phenylacetyl)-2-carbamoyl-4-(2-methylphenyl)piperazine

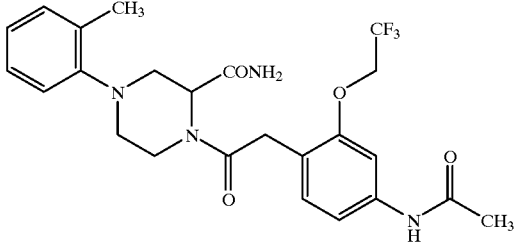

To a solution of 1-(4-amino-2-(2,2,2-trifluoroethoxy)-phenylacetyl)-2-carbamoyl-4-(2-methylphenyl)piperazine (0.10 g, 0.18 mmol) from Example 6 in CH₂Cl₂ (10 mL) at 0° C. was added acetyl chloride (0.014 mL, 0.2 mmol) and DIEA (0.04 mL, 0.22 mmol). The solution was stirred at ambient temperature for 2 h and the solvent was removed under reduced pressure. The residue was dissolved in EtOAc (100 mL) and washed with 0.25 M aqueous citric acid (50 mL), H₂O (25 mL), and saturated aqueous NaHCO₃ (75 mL). The organic phase was dried (MgSO₄), filtered, and the solvent was removed under reduced pressure. The residue was purified by preparative reverse phase HPLC using a water:acetonitrile gradient containing 0.1% TFA. The product-containing fractions were lyophilized to give the TFA salt of title compound as an amorphous solid.

HPLC retention time=8.28 min (method A) TLC $R_f$=0.3 (95:5 CH₂Cl₂:MeOH); FAB MS: m/z=493 (M⁺+H); combustion analysis: $C_{24}H_{27}F_3N_4O_4$, 0.45 TFA, 0.9 H₂O ; Calculated C, 53.40; H, 5.26; N, 10.00; Found C, 53.41; H, 5.25; N, 9.79

EXAMPLE 16

1-(4-chloro-2-(2,2,2-trifluoroethoxy)phenylacetyl)-2-carbamoyl-4-(2-methylphenyl)piperazine

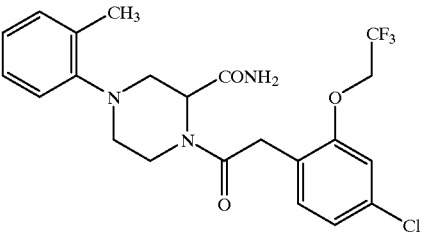

4-Chloro-2-(2,2,2-trifluoroethoxy)phenylacetic acid was prepared from 4-chloro-2-hydroxytoluene using procedures analogous to those given in Steps 1–4 of Example 21 and then coupled to 2-carbamoyl-4-(2-methylphenyl)piperazine using a procedure analogous to that given in Step 5 of Example 21. The product was purified by preparative reverse phase HPLC using a water:acetinitrile gradient containing 0.1% TFA. The product-containing fractions were lyophilized to give the TFA salt of the title compound as an amorphous solid.

HPLC retention time=23.5 min (method C) TLC $R_f$=0.5 (95:5:0.5 CH₂Cl₂:MeOH:NH₄OH); FAB MS: m/z=470

(M++H); combustion analysis: $C_{22}H_{23}ClF_3N_3O_3$, 0.8 TFA; Calculated C, 50.51; H, 4.28; N, 7.49; Found C, 50.57; H, 4.28; N, 7.39

EXAMPLE 17

1-(5-chloro-2-(2,2,2-trifluoroethoxy)phenylacetyl)-2-carbamoyl-4-(2-methylphenyl)piperazine

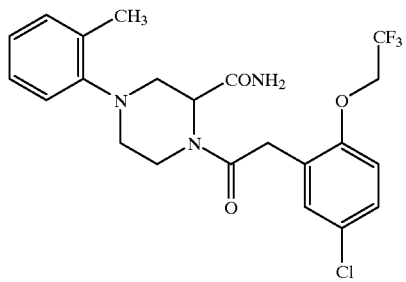

5-Chloro-2-(2,2,2-trifluoroethoxy)phenylacetic acid was prepared from 5-chloro-2-hydroxytoluene using procedures analogous to those given in Steps 1–4 of Example 21 and then coupled to 2-carbamoyl-4-(2-methylphenyl)piperazine using a procedure analogous to that given in Step 5 of Example 21. The product was purified by preparative reverse phase HPLC using a water:acetinitrile gradient containing 0.1% TFA. The product-containing fractions were lyophilized to give the TFA salt of the title compound as an amorphous solid.

HPLC retention time=23.3 min (method C) TLC $R_f$=0.6 (95:5:0.5 $CH_2Cl_2$:MeOH:$NH_4OH$); FAB MS: m/z=470 (M++H); combustion analysis: $C_{22}H_{23}ClF_3N_3O_3$, 0.75 TFA, 0.05 $H_2O$; Calculated C, 50.73; H, 4.32; N, 7.55; Found C, 50.72; H, 4.24; N, 7.44

EXAMPLE 18

1-(4-trifluoromethyl-2-(2,2,2-trifluoroethoxy)phenylacetyl)-2-carbamoyl-4-(2-methylphenyl)piperazine

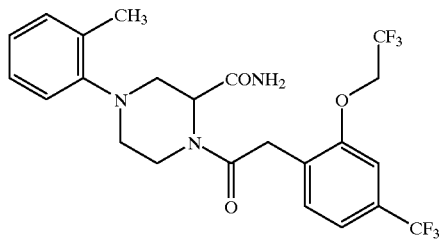

4-Trifluoromethyl-2-(2,2,2-trifluoroethoxy)phenylacetic acid was prepared from 2-fluoro-5-trifluoromethylacetophenone using procedures analogous to those given in Steps 1–3 of Example 19 and then coupled to 2-carbamoyl-4-(2-methylphenyl)piperazine using a procedure analogous to that given in Step 4 of Example 19. The product was purified by pressurized silica gel column chromatography using 95:5 $CH_2Cl_2$:MeOH as eluant. The title compound was obtained as an amorphous solid.

HPLC retention time=10.1 min (method A) TLC $R_f$=0.5 (95:5 $CH_2Cl_2$:MeOH); FAB MS: m/z=504 (M++H); combustion analysis: $C_{23}H_{23}F_6N_3O_3$, 1.4 $CH_2Cl_2$ ; Calculated C, 47.09; H, 4.18; N, 6.75; Found C, 47.20; H, 3.74; N, 7.19

EXAMPLE 19

1-(5-trifluoromethyl-2-(2,2,2-trifluoroethoxy)phenylacetyl)-2-carbamoyl-4-(2-methylphenyl)piperazine

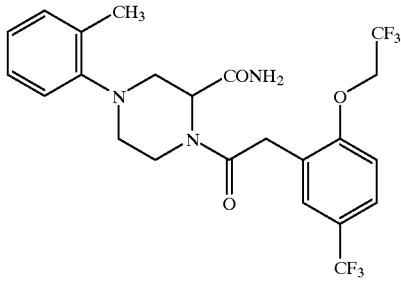

Step 1. To a stirred solution of 2,2,2-trifluoroethanol (0.53 mL, 7.3 mmol) in THF (20 mL) at 0° C. was added potassium tert-butoxide (7.3 mL of a 1.0 M solution in THF, 7.3 mmol). The mixture was stirred at 0° C. for 10 min and 2-fluoro-5-trifluoromethyl-acetophenone (1.0 g, 4.9 mmol; HPLC retention time=8.7 min (method A)) was added. The mixture was stirred at 0° C. for 15 min and then at ambient temperature for 5 h. The solvent was removed under reduced pressure and the residue was partitioned between EtOAc (100 mL) and saturated aqueous $NaHCO_3$ (2×50 mL). The organic phase was dried ($MgSO_4$), filtered, and the solvent was removed under reduced pressure to give 2-(2,2,2-trifluoroethoxy)-5-trifluoromethylacetophenone as a gum (HPLC retention time=10.0 min (method A)).

Step 2. To a stirred solution of 2-(2,2,2-trifluoroethoxy)-5-trifluoromethylacetophenone (0.97 g, 3.4 mmol) from Step 1 above in MeOH (17 mL) was added trimethyl orthoformate (1.1 mL, 1.1 mmol) and thallium trinitrate trihydrate (1.5 g, 3.4 mmol). The mixture was stirred at ambient temperature for 48 h. The precipitate which had formed was removed by filtration and the filtrate solvent was removed under reduced pressure. The residue was partitioned between EtOAc (100 mL) and saturated aqueous $NaHCO_3$ (2×50 mL). The organic phase was dried ($MgSO_4$), filtered, and the solvent was removed under reduced pressure to give methyl 2-(2,2,2-trifluoroethoxy)-5-trifluoromethylphenylacetate as a gum (HPLC retention time=10.0 min (method A)).

Step 3. To a stirred solution of methyl 2-(2,2,2-trifluoroethoxy)-5-trifluoromethylphenylacetate (1.07 g, 3.5 mmol) from Step 2 above in THF (8 mL) and water (2 mL) was added LiOH (0.20 g, 4.8 mmol). The mixture was stirred at ambient temperature for 24 h. The reaction was acidified to pH 2 with 5 N aqueous HCl and the solvents were removed under reduced pressure. The residue was purified by pressurized silica gel column chromatography using a gradient elution of 0–50% MeOH:$CH_2Cl_2$ to give 2-(2,2,2-trifluoroethoxy)-5-trifluoromethylphenylacetic acid as a gum (HPLC retention time=8.7 min (method A)).

Step 4. To a stirred solution of 2-(2,2,2-trifluoroethoxy)-5-trifluoromethylphenylacetic acid (0.10 g, 0.33 mmol) from Step 3 above, 1-2-carbamoyl-4-(2-methylphenyl)piperazine (0.08 g, 0.36 mmol) from Step 4 of Example 1, and HOBT (0.06 g, 0.4 mmol) in DMF (5 mL) was added EDC (0.10 g, 0.5 mmol) and DIEA (0.088 mL, 0.5 mmol). The mixture was stirred at ambient temperature for 14 h. The solvent was removed under reduced pressure and the residue was purified by pressurized silica gel column chromatography using 5:95 MeOH:CH$_2$Cl$_2$ as eluant. The product-containing fractions were evaporated under reduced pressure to give the title compound as an amorphous powder.

HPLC retention time=9.96 min (method A) TLC R$_f$=0.3 (5:95 MeOH:CH$_2$Cl$_2$); FAB MS: m/z=504 (M$^+$+H), 0.45 CH$_2$Cl$_2$, 0.05 H$_2$O; combustion analysis: C$_{23}$H$_{23}$F$_6$N$_3$O$_3$, 0.45 CH$_2$Cl$_2$, 0.05 H$_2$O; Calculated C, 51.91; H, 4.46; N, 7.75; Found C, 51.94; H, 4.33; N, 7.67

EXAMPLE 20

1-(4-(2-pyridinyloxy)-2-(2,2,2-trifluoroethoxy) phenylacetyl)-2-carbamoyl-4-(2-methylphenyl) piperazine

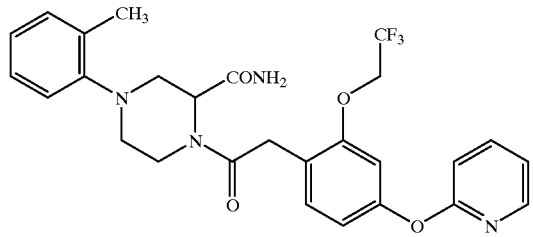

Step 1. To a stirred solution of 2-hydroxy-4-fluoroacetophenone (10 g, 65 mmol) in DMF (300 mL) at 0° C. was added 2,2,2-trifluoroethyl trifluoromethanesulfonate (25 g, 120 mmol) and Cs$_2$CO$_3$ (39 g, 120 mmol). The mixture was stirred at 0° C. for 2 h and then at ambient temperature for 14 h. EtOAc (300 mL) was added and the solid was removed by filtration. The filtrate solvents were removed under reduced pressure and the residue was partitioned between EtOAc (250 mL) and saturated aqueous NaHCO$_3$ (2×100 mL). The organic phase was dried (MgSO$_4$), filtered, and the solvent was removed under reduced pressure. The residue was purified by pressurized silica gel column chromatography using 5% EtOAc:hexanes as eluant to give 2-(2,2,2-trifluoroethoxy)-4-fluoroacetophenone as a colorless oil (HPLC retention time= 8.8 min (method A); TLC R$_f$=0.55 (20% EtOAc:hexanes)).

Step 2. To a stirred solution of 2-(2,2,2-trifluoroethoxy)-4-fluoroacetophenone (0.40 g, 1.7 mmol) from Step 1 above in DMF (10 mL) was added 2-hydroxypyridine (0.24 g, 2.5 mmol) and Cs$_2$CO$_3$ (1.1 g, 3.4 mmol). The mixture was heated to 50° C. and stirred for 14 h. The solids were removed by filtration and the filtrate solvent was removed under reduced pressure. The residue was partitioned between EtOAc and water. The organic phase was dried (MgSO$_4$), filtered, and the solvent was removed under reduced pressure to give 2-(2,2,2-trifluoroethoxy)- 4-(2-pyridyloxy)acetophenone as an amorphous solid (HPLC retention time=6.6 min (method A)).

Step 3. To a stirred solution of 2-(2,2,2-trifluoroethoxy)-4-(2-pyridyloxy)acetophenone (0.48 g, 1.5 mmol)) from Step 2 above in MeOH (8 mL) was added trimethyl orthoformate (0.50 mL, 4.5 mmol) and thallium trinitrate trihydrate (0.68 g, 1.5 mmol). The mixture was stirred at ambient temperature for 14 h. The precipitate that had formed was removed by filtration and the filtrate solvent was removed under reduced pressure. The residue was partitioned between EtOAc (75 mL) and saturated aqueous NaHCO$_3$ (2×50 mL). The organic phase was dried (MgSO$_4$), filtered, and the solvent was removed under reduced pressure to give methyl 2-(2,2,2-trifluoroethoxy)-4-(2-pyridyloxy) phenylacetate as an oil (HPLC retention time=6.6 min (method A)).

Step 4. To a stirred solution of methyl 2-(2,2,2-trifluoroethoxy)-4-(2-pyridyloxy)phenylacetate (0.45 g, 1.3 mmol) from Step 3 above in THF (4 mL) and water (1 mL) was added LiOH·H$_2$O (0.065 g, 1.5 mmol). The mixture was stirred at ambient temperature for 14 h. The solution was adjusted to pH 3 by the addition of 5 N aqueous HCl and the solvents were removed under reduced pressure. The residue was purified by pressurized silica gel column chromatography using a gradient elution of 0–20% MeOH:CH$_2$Cl$_2$ to give 2-(2,2,2-trifluoroethoxy)-4-(2-pyridyloxy)-phenylacetic acid as a gum (HPLC retention time=5.4 min (method A)).

Step 5. To a stirred solution of 2-(2,2,2-trifluoroethoxy)-4-(2-pyridyloxy)phenylacetic acid (0.10 g, 0.31 mmol) from Step 4 above and 2-carbamoyl-4-(2-methylphenyl) piperazine (0.08 g, 0.35 mmol) from Step 4 of Example 1 in DMF (2 mL) was added HOBT (0.06 g, 0.35 mmol), EDC (0.10 g, 0.5 mmol), and DIEA (0.09 mL, 0.5 mmol). The solution was stirred at ambient temperature for 14 h and the solvent was removed under reduced pressure. The residue was partitioned between EtOAc (50 mL) and saturated aqueous NaHCO$_3$ (2×25 mL). The organic phase was dried (MgSO$_4$), filtered, and the solvent was removed under reduced pressure. The residue was purified by pressurized silica gel column chromatography using 95:5 CH$_2$Cl$_2$:MeOH as eluant. The product-containing fractions were evaporated under reduced pressure to give the title compound as an amorphous solid.

HPLC retention time=7.96 min (method A) TLC R$_f$=0.25 (95:5 CH$_2$Cl$_2$:MeOH); FAB MS: m/z=529 (M$^+$+H); combustion analysis: C$_{27}$H$_{27}$F$_3$N$_4$O$_4$, 1.15 CH$_2$Cl$_2$ ; Calculated C, 53.99; H, 4.72; N, 8.95; Found C, 54.06; H, 4.52; N, 8.68

EXAMPLE 21

1-(3-chloro-2-(2,2,2-trifluoroethoxy)phenylacetyl)-2-carbamoyl-4-(2-methylphenyl)piperazine

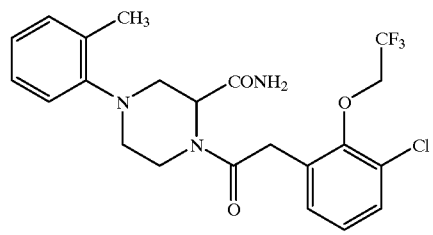

Step 1. To a solution of 2-hydroxy-3-chlorotoluene (5 g, 35 mmol) in DMF (75 mL) at 0° C. was added 2,2,2-trifluoroethoxy trifluoromethylsulfonate (16 g, 70 mmol) and Cs$_2$CO$_3$ (22 g, 68 mmol). The mixture was stirred at 0° C. for 3 h and then at ambient temperature for 14 h. The solvent was removed under reduced pressure. The residue was partitioned between EtOAc (150 mL) and water (3×75 mL). The organic phase was dried (MgSO$_4$), filtered, and the solvent was removed under reduced pressure. The residue was purified by pressurized silica gel column chromatography using 1:4 EtOAc:hexanes as eluant to give 2-(2,2,2-trifluoroethoxy)-3-chlorotoluene as an oil.

Step 2. To a stirred solution of 2-(2,2,2-trifluoroethoxy)-3-chlorotoluene (2.4 g, 11 mmol) from Step 1 above in CCl$_4$ (40 mL) was added NBS (2.1 g, 11 mmol) and AIBN (1.8 g, 11 mmol). The mixture was refluxed for 8 h. The solvent was removed under reduced pressure and the residue was partitioned between EtOAc and saturated aqueous NaHCO$_3$. The organic phase was dried (MgSO₄), filtered, and the solvent was removed under reduced pressure. The residue was purified by silica gel column chromatography using hexanes as eluant. 2-(2,2,2-trifluoroethoxy)-3-chlorobenzyl bromide was obtained as an oil (HPLC retention time=22.3 min (method D)).

Step 3. To a solution of 2-(2,2,2-trifluoroethoxy)-3-chlorobenzyl bromide (1.6 g, 5.4 mmol) from Step 2 above in DMF (12 mL) was added NaCN (0.28 g, 5.7 mmol). The solution was stirred at ambient temperature for 14 h. The solvent was removed under reduced pressure and the residue was partitioned between EtOAc and saturated aqueous NaHCO₃. The organic phase was dried (MgSO₄), filtered, and the solvent was removed under reduced pressure. The residue was purified by pressurized silica gel column chromatography using a gradient elution of 5–20% EtOAc:hexanes to give 2-(2,2,2-trifluoroethoxy)-3-chlorophenylacetonitrile as a colorless oil.

Step 4. 2-(2,2,2-trifluoroethoxy)-3-chlorophenylacetonitrile (1.2 g, 5.1 mmol) from Step 3 above was refluxed in a 2:1 mixture of acetic acid and concentrated aqueous HCl (25 mL) for 12 h. The solvents were removed under reduced pressure and the residue was partitioned between EtOAc and water. The organic phase was washed with water, dried (MgSO₄), filtered, and the solvent was removed under reduced pressure to give 2-(2,2,2-trifluoroethoxy)-3-chlorophenylacetic acid as an oil.

Step 5. To a stirred solution of 2-(2,2,2-trifluoroethoxy)-3-chlorophenylacetic acid (0.14 g, 0.53 mmol) from Step 4 above, 2-carbamoyl-4-(2-methylphenyl)piperazine (0.12 g, 0.53 mmol) from Step 4 of Example 1, and HOBT (0.08 g, 0.53 mmol) in DMF (5 mL) was added EDC (0.15 g, 0.8 mmol) and DIEA (0.14 mL, 0.8 mmol). The mixture was stirred at ambient temperature for 14 h. The solvent was removed under reduced pressure and the residue was purified by preparative reverse phase HPLC using a H₂O:CH₃CN gradient containing 0.1% TFA. The product-containing fractions were lyophilized to give the title compound as an amorphous powder.

HPLC retention time=24.6 min (method C) TLC R$_f$=0.5 (95:5:0.5 CH₂Cl₂:MeOH:NH₄OH); FAB MS: m/z=470 (M⁺+H); combustion analysis: C₂₂H₂₃ClF₃N₃O₃, 0.75 TFA; Calculated C, 50.82; H, 4.31; N, 7.57; Found C, 50.80; H, 4.21; N, 7.61

EXAMPLE 22

1-(2-(2,2,2-trifluoroethoxy)phenylacetyl)-4-(3-trifluoromethylphenyl)-piperazine

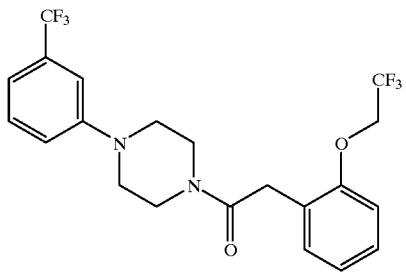

The title compound was prepared and purified using the procedure given in Example 12 using 3-trifluoromethylphenyl-piperazine in place of 2-methoxyphenylpiperazine.

HPLC retention time=11.6 min (method D) TLC R$_f$=0.62 (1:2 EtOAc:hexanes); FAB MS: m/z=xx (M⁺+H; combustion analysis: C₂₁H₂₀F₆N₂O₂), 0.1 ether; Calculated C, 56.64; H, 4.66; N, 6.17; Found C, 56.95; H, 4.75; N, 5.95

EXAMPLE 23

1-(2-(2,2,2-trifluoroethoxy)phenylacetyl)-4-(2-pyrazinyl)piperazine

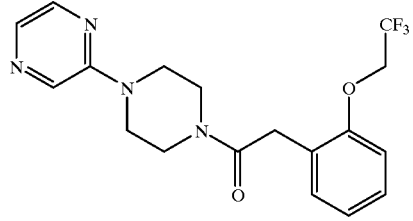

The title compound was prepared and purified using the procedure given in Example 12 using 2-pyrazinylpiperazine in place of 2-methoxyphenylpiperazine.

HPLC retention time=7.5 min (method D) TLC R$_f$=0.34 (1:1 EtOAc:hexanes); FAB MS: m/z=381 (M⁺+H); combustion analysis: C₁₈H19F₃N₄O₂; Calculated C, 56.91; H, 5.12; N, 14.59; Found C, 57.27; H, 5.06; N, 14.91

EXAMPLE 24

1-(2-(2,2,2-trifluoroethoxy)phenylacetyl)-4-(2-pyrimidinyl)piperazine

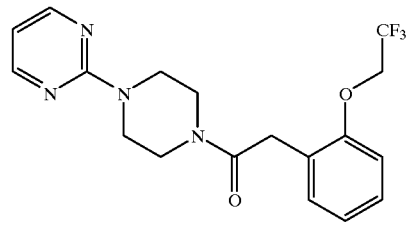

The title compound was prepared and purified using the procedure given in Example 12 using 2-pyrimidinylpiperazine in place of 2-methoxyphenylpiperazine.

HPLC retention time=8.2 min (method D) TLC R$_f$=0.42 (1:1 EtOAc:hexanes); FAB MS: m/z=381 (M⁺+H); combustion analysis: C₁₈H19F₃N₄O₂ ; Calculated C, 56.84; H, 5.03; N, 14.73; Found C, 57.07; H, 5.06; N, 14.53

EXAMPLE 25

1-(2-(2,2,2-trifluoroethoxy)phenylacetyl)-4-(2,6-dimethylphenyl)-piperazine

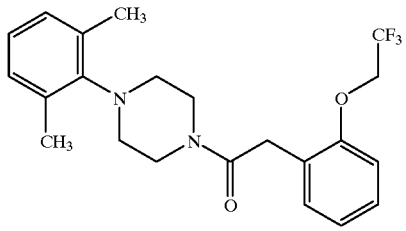

The title compound was prepared and purified using the procedure given in Example 12 using 2,6-dimethylphenylpiperazine in place of 2-methoxyphenylpiperazine.

HPLC retention time=12 min (method D) TLC $R_f$=0.27 (1:2 EtOAc:hexanes); FAB MS: m/z=407 (M$^+$+H); combustion analysis: $C_{22}H_{25}F_3N_2O_2$; Calculated C, 65.01; H, 6.20; N, 6.89; Found C, 64.69; H, 6.20; N, 6.69

EXAMPLE 26

1-(4-(1-triazolyl)-2-(2,2,2-trifluoroethoxy)phenylacetyl)-2-carbamoyl-4-(2-methylphenyl)piperazine

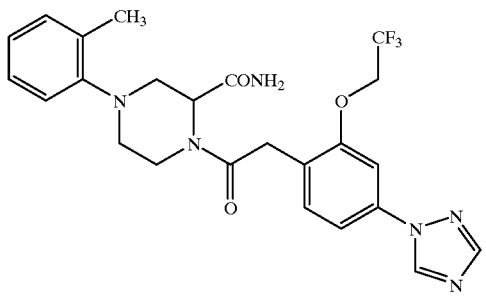

Step 1. To a stirred solution of 2-(2,2,2-trifluoroethoxy)-4-fluoroacetophenone (0.40 g, 1.7 mmol) from Step 1 of Example 20 in DMF (10 mL) was added 1,2,4-triazole (0.18 g, 2.5 mmol) and $Cs_2CO_3$ (1.1 g, 3.4 mmol). The mixture was heated to 50° C. and stirred for 24 h. The solids were removed by filtration and the filtrate solvent was removed under reduced pressure. The residue was partitioned between EtOAc and water. The organic phase was dried (MgSO$_4$), filtered, and the solvent was removed under reduced pressure. The residue was purified by pressurized silica gel column chromatography using a gradient elution of 10–40% EtOAc:hexanes to give 2-(2,2,2-trifluoroethoxy)-4-(1-triazolyl)acetophenone as an amorphous solid (HPLC retention time=7.6 min (method A)).

Step 2. To a stirred solution of 2-(2,2,2-trifluoroethoxy)-4-(1-triazolyl)acetophenone (0.45 g, 1.6 mmol)) from Step 1 above in MeOH (8 mL) was added trimethyl orthoformate (0.52 mL, 4.8 mmol) and thallium trinitrate trihydrate (0.71 g, 1.6 mmol). The mixture was stirred at ambient temperature for 14 h. The precipitate that had formed was removed by filtration and the filtrate solvent was removed under reduced pressure. The residue was partitioned between EtOAc (75 mL) and saturated aqueous NaHCO$_3$ (2×50 mL). The organic phase was dried (MgSO$_4$), filtered, and the solvent was removed under reduced pressure to give methyl 2-(2,2,2-trifluoroethoxy)- 4(1-triazolyl)phenylacetate as an oil (HPLC retention time=7.6 min (method A)).

Step 3. To a stirred solution of methyl 2-(2,2,2-trifluoroethoxy)-4-(1-triazolyl)phenylacetate (0.54 g, 1.7 mmol) from Step 2 above in THF (10 mL) and water (2.5 mL) was added LiOH·H$_2$O (0.11 g, 2.6 mmol). The mixture was stirred at ambient temperature for 14 h. The solution was adjusted to pH 2 by the addition of 5 N aqueous HCl and the solvents were removed under reduced pressure to give 2-(2,2,2-trifluoroethoxy)-4-(1-triazolyl)phenylacetic acid was obtained as a gum (HPLC retention time=6.0 min (method A)).

Step 4. To a stirred solution of 2-(2,2,2-trifluoroethoxy)-4-(1-triazolyl)phenylacetic acid (0.10 g, 0.33 mmol) from Step 3 above and 2-carbamoyl-4-(2-methylphenyl)piperazine (0.08 g, 0.35 mmol) from Step 4 of Example 1 in DMF (2 mL) was added HOBT (0.06 g, 0.35 mmol), EDC (0.10 g, 0.5 mmol), and DIEA (0.09 mL, 0.5 mmol). The solution was stirred at ambient temperature for 14 h and the solvent was removed under reduced pressure. The residue was partitioned between EtOAc (50 mL) and 0.25 M aqueous citric acid (25 mL). The organic phase was separated and washed with H$_2$O (10 mL), and saturated aqueous NaHCO$_3$ (25 mL). The organic phase was dried (MgSO$_4$), filtered, and the solvent was removed under reduced pressure. The residue was purified by preparative reverse phase HPLC using a water:acetonitrile mobil phase containing 0.1% TFA. The TFA salt of the title compound was obtained an amorphous solid by lyophilization of the product-containing fractions.

HPLC retention time=8.17 min (method A) TLC $R_f$=0.2 (95:5 CH$_2$Cl$_2$:MeOH); FAB MS: m/z=503 (M$^+$+H), 2.0 TFA; combustion analysis: $C_{24}H_{25}F_3N_6O_3$, 2.0 TFA; Calculated C, 46.03; H, 3.72; N, 11.50; Found C, 46.00; H, 3.51; N, 11.55

EXAMPLE 27

1-(2-(2,2,2-trifluoroethoxy)phenylacetyl)-4-(4-fluorophenyl)piperazine

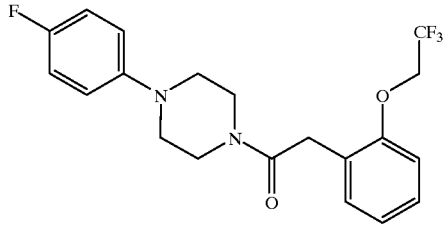

The title compound was prepared and purified using the procedure given in Example 12 using 4-fluorophenylpiperazine in place of 2-methoxyphenylpiperazine.

HPLC retention time=10.3 min (method D) TLC $R_f$=0.59 (1:2 EtOAc:hexanes); FAB MS: m/z=397 (M$^+$+H); combustion analysis: $C_{20}H_{20}F_4N_2O_2$; Calculated C, 60.60; H, 5.09; N, 7.07; Found C, 60.50; H, 5.16; N, 7.16

EXAMPLE 28

1-(4-fluoro-2-(2,2,2-trifluoroethoxy)phenylacetyl)-2-carbamoyl-4-(2-methylphenyl)piperazine:

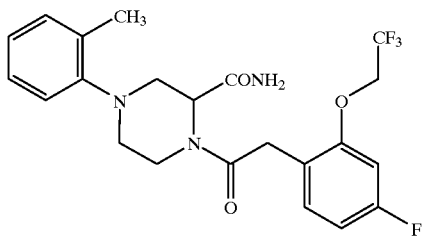

Step 1. To a stirred solution of NaOH (2.0 g, 50 mmol) in water (15 mL) at 0° C. was added bromine (3.0 g, 19 mmol). The solution was stirred for 10 min and a solution of 2-(2,2,2-trifluoroethoxy)-4-fluoroacetophenone (1.5 g, 6.4 mmol)) from Step 1 of Example 20 in dioxane (25 mL) was added dropwise over 15 min. The mixture was stirred at 0° C. for 15 min, at ambient temperature for 12 h ,and then at reflux for 1.5 h. The mixture was cooled to 0° C. and acidified to pH 2 by the addition of 6 N aqueous HCl. The mixture was concentrated under reduced pressure and then extracted with $CH_2Cl_2$ (2×75 mL). The combined organic extracts were dried ($MgSO_4$), filtered, and the solvent was removed under reduced pressure to give 2-(2,2,2-trifluoroethoxy)-4-fluorobenzoic acid as an amorphous solid (HPLC retention time=7.1 min (method A)).

Step 2. To a stirred solution of 2-(2,2,2-trifluoroethoxy)-4-fluorobenzoic acid (2.0 g, 8.4 mmol) from Step 1 above in THF (25 mL) at 0° C. was added $BH_3$.THF complex (25 mL of a 1.0 M solution in THF, 25 mmol). The mixture was stirred at 0° C. for 30 min and then at ambient temperature for 6 h. Aqueous NaOH (20 mL of a 4 N solution, 80 mmol) was added and the solvents were removed under reduced pressure. The residue was partitioned between EtOAc (100 mL) and water (2×50 mL). The organic phase was dried ($MgSO_4$), filtered, and the solvent was removed under reduced pressure to give 2-(2,2,2-trifluoroethoxy)-4-fluorobenzyl alcohol as an oil (HPLC retention time=7.3 min (method A)).

Step 3. To a stirred solution of 2-(2,2,2-trifluoroethoxy)-4-fluorobenzyl alcohol (1.2 g, 5.3 mmol) from Step 2 above in ether (30 mL) was added $CBr_4$ (3.0 g, 9.2 mmol) and triphenylphosphine (2.4 g, 9.2 mmol). The mixture was stirred at ambient temperature for 14 h. Triphenylphosphine oxide was removed by filtration and the filtrate was diluted with EtOAc (50 mL) and washed with saturated aqueous $NaHCO_3$ (2×50 mL). The organic phase was dried ($MgSO_4$), filtered, and the solvent was removed under reduced pressure. The residue was purified by pressureized silica gel column chromatography using a gradient elution of 0–5% EtOAc:hexanes to give 2-(2,2,2-trifluoroethoxy)-4-fluorobenzyl bromide as a colorless oil (HPLC retention time=10.4 min (method A)).

Step 4. To a stirred solution of 2-(2,2,2-trifluoroethoxy)-4-fluorobenzyl bromide (0.80 g, 2.7 mmol) from Step 3 above in DMF (14 mL) was added NaCN (0.20 g, 4.0 mmol). The mixture was stirred at ambient temperature for 14 h. The solvent was removed under reduced pressure and the residue was partitioned between EtOAc (100 mL) and saturated aqueous $NaHCO_3$ (2×50 mL). The organic phase was dried ($MgSO_4$), filtered, and the solvent was removed under reduced pressure to give 2-(2,2,2-trifluoroethoxy)-4-fluorophenyl-acetonitrile as an oil (HPLC retention time=8.7 min (method A)).

Step 5. To a stirred solution of 2-(2,2,2-trifluoroethoxy)-4-fluorophenylacetonitrile (0.60 g, 2.7 mmol) from Step 4 above in acetic acid (10 mL) was added 12 N aqueous HCl (5 mL). The mixture was refluxed for 4 h. The solvents were removed under reduced pressure and the residue was partitioned between EtOAc (100 mL) and water (2–50 mL). The organic phase was dried ($MgSO_4$), filtered, and the solvent was removed under reduced pressure to give 2-(2,2,2-trifluoroethoxy)-4-fluorophenylacetic acid as an amorphous solid (HPLC retention time=7.5 min (method A)).

Step 6. To a stirred solution of 2-(2,2,2-trifluoroethoxy)-4-fluorophenylacetic acid (0.15 g, 0.60 mmol) from Step 5 above and 2-carbamoyl-4-(2-methylphenyl)piperazine (0.13 g, 0.66 mmol) from Step 4 of Example 1 in DMF (3 mL) was added HOBT (0.11 g, 0.78 mmol), EDC (0.17 g, 0.9 mmol), and DIEA (0.16 mL, 0.9 mmol). The solution was stirred at ambient temperature for 14 h and the solvent was removed under reduced pressure. The residue was partitioned between EtOAc (50 mL) and 0.25 M aqueous citric acid (25 mL). The organic phase was separated and washed with $H_2O$ (10 mL) and saturated aqueous $NaHCO_3$ (25 mL). The organic phase was dried ($MgSO_4$), filtered, and the solvent was removed under reduced pressure. The residue was purified by pressurized silica gel column chromatography using 5:95 MeOH:$CH_2Cl_2$ as eluant. Evaporation of the product-containing fractions gave the title compound as an amorphous solid. HPLC retention time=9.16 min (method A) TLC $R_f$=0.25 (5:95 MeOH:$CH_2Cl_2$); FAB MS: m/z=454 ($M^+$+H), 0.4 $CH_2Cl_2$ ; combustion analysis: $C_{22}H_{23}F_4N_3O_3$, 0.4 $CH_2Cl_2$; Calculated C, 57.43; H, 5.12; N, 8.97; Found C, 57.44; H, 4.89; N, 9.22

EXAMPLE 29

1-(2-(2,2,2-trifluoroethoxy)phenylacetyl)-4-(2-naphthyl)piperazine

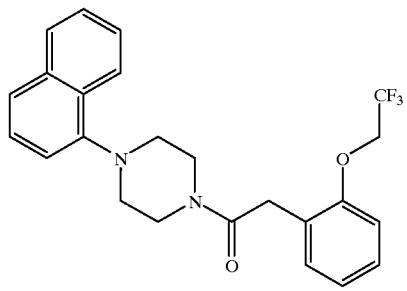

The title compound was prepared and purified using the procedure given in Example 12 using 2-naphthylpiperazine in place of 2-methoxyphenylpiperazine.

HPLC retention time=12.1 min (method D) TLC $R_f$=0.63 (1:2 EtOAc:hexanes); FAB MS: m/z=429 ($M^+$+H); combustion analysis: $C_{24}H_{23}F_3N_2O_2$ ; Calculated C, 67.28; H, 5.41; N, 6.54; Found C, 67.33; H, 5.55; N, 6.38

EXAMPLE 30

1-(2-(2,2,2-trifluoroethoxy)phenylacetyl)-2-N-methylcarbamoyl-4-(2-methylphenyl)piperazine

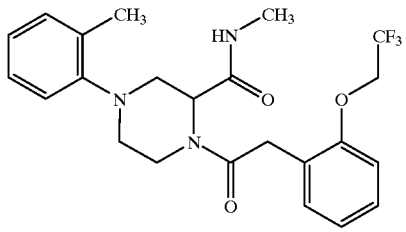

Step 1. To a solution of 1-benzyl-2-carbamoyl-4-(2-methylphenyl)piperazine (1.5 g, 4.8 mmol) from Step 3 of Example 1 in acetonitrile (125 mL) was added di-tert-butyldicarbonate (3.2 g, 14.6 mmol), and DMAP (0.29 g, 2.4 mmol). The mixture was stirred at ambient temperature for 24 h. The solvent was removed under reduced pressure and the residue was purified by pressurized silica gel column chromatography using 95:5 hexanes:EtOAc as eluant to give 1-benzyl-2-N,N-di(tert-butyloxycarbonyl)carbamoyl-4-(2-methylphenyl)piperazine as a dense gum (TLC Rf=0.59 (85:15 hexanes:EtOAc)).

Step 2. Into a solution of 1-benzyl- 2-N,N-di(tert-butyloxycarbonyl)carbamoyl-4-(2-methylphenyl)piperazine from the previous step (0.20 g, 0.39 mmol) in EtOH (5 mL) at 0° C. was bubbled methylamine gas for 10 min. The mixture was stirred at 0° C. for 2 h, and the solvent was evaporated under reduced pressure. The residue was purified by pressureized silica gel column chromatography using 4:1 hexanes:EtOAc as eluant to give 1-benzyl-2-N-methylcarbamoyl-4-(2-methylphenyl)piperazine as an amorphous solid (TLC Rf=0.10 (85:15 hexanes:EtOAc)).

Step 3. To a solution of 1-benzyl-2-N-methylcarbamoyl-4-(2-methylphenyl)piperazine from the previous step (0.11 g, 0.34 mmol) in EtOH (3 mL) was added 10% palladium on carbon (20 mg). The mixture was stirred at ambient temperature und 1 atmohere of hydrogen gas for 3 h. The hydrogen was purged with argon and the catalyst was removed by filtration through celite. The solvent was removed under reduced pressure to give 2-N-methylcarbamoyl-4-(2-methylphenyl)piperazine as an oil (TLC Rf=0.46 (96:4:0.4 $CH_2Cl_2$:MeOH:$NH_4OH$)).

Step 4. 2-N-methylcarbamoyl-4-(2-methylphenyl)-piperazine from the previous step and 2-(2,2,2-trifluoroethoxy)-phenylacetic acid from Step 2 of Example 8 were coupled using the procedure given in Example 12. The crude product was purified by pressurized silica gel column chromatography using 3:2 EtOAc:hexanes as eluant. The title compound was obtained as an amorphous solid.

HPLC retention time=9.2 min (method A) TLC $R_f$=0.3 (3:2 EtOAc:hexanes); FAB MS: m/z=450 (M$^+$+H), 0.15 EtOAc, 0.35 $H_2O$ ; combustion analysis: $C_{23}H_{26}F_3N_3O_3$, 0.15 EtOAc, 0.35 $H_2O$ ; Calculated C, 60.43; H, 6.00; N, 8.96; Found C, 60.43; H, 5.93; N, 8.95

EXAMPLE 31

1-(2-(2,2,2-trifluoroethoxy)phenylacetyl)-2-N-ethylcarbamoyl-4-(2-methylphenyl)piperazine

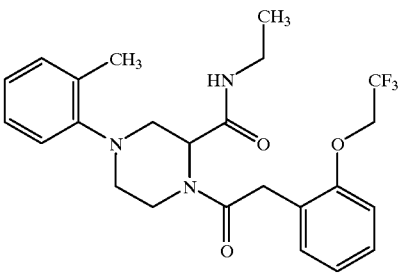

The title compound was prepared using the methods given in Example 30, except that ethylamine was used in place of methylamine in Step 2. The crude product was purified by pressurized silica gel column chromatography using 3:2 EtOAc:hexanes as eluant to give the title compound as an amorphous solid.

HPLC retention time=9.7 min (method A) TLC $R_f$=0.14 (7:3 hexanes:EtOAc); FAB MS: m/z=464 (M$^+$+H); combustion analysis: $C_{24}H_{28}F_3N_3O_3$, 0.1 $H_2O$; Calculated C, 61.94; H, 6.11; N, 9.03; Found C, 61.95; H, 6.11; N, 9.00

EXAMPLE 32

1-(2-(2,2,2-trifluoroethoxy)phenylacetyl)-2-N,N-dimethylcarbamoyl-4-(2-methylphenyl)piperazine

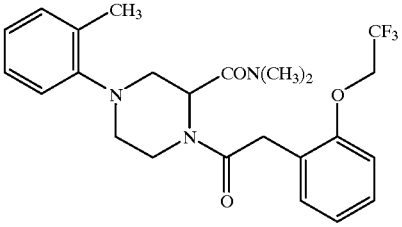

Step 1. To a solution of 1-benzyl-2-carbamoyl-4-(2-methylphenyl)piperazine (0.10 g, 0.32 mmol) from Step 3 of Example 1 in DMF (1 mL) at 0° C. was added NaH (0.025 g of a 60% dispersion in mineral oil, 1.0 mmol). The mixture was stirred at 0° C. for 1 h and then iodomethane (0.061 mL, 1.0 mmol) was added and the mixture was stirred at ambient temperature for 4 h. More NaH was added (0.012 g, 0.50 mmol) and the mixture was warmed to 50° C. for 30 min. The mixture was cooled to ambient temperature and additional iodomethane (0.020 mL, 0.33 mmol) was added. The mixture was stirred at ambient temperature for 18 h. Saturated aqueous NaHCO$_3$ (1 mL) was added and the solvents were removed under reduced pressure. The reisude was purified by pressurized silica gel column chromatography using 3:1 hexanes:EtOAc as eluant to give 1-benzyl-2-N,N-dimethylcarbamoyl-4-(2-methylphenyl)piperazine as a colorless oil (TLC $R_f$=0.20 (3:1 hexanes:EtOAc)).

Steps 2–3. The benzyl group in 1-benzyl-2-N,N-dimethylcarbamoyl-4-(2-methylphenyl)piperazine from the previous step was removed using the procedure given in Step 3 of Example 30, and the product, 2-N,N-dimethylcarbamoyl-4-(2-methylphenyl)-piperazine, was coupled to 2-(2,2,2-trifluoroethoxy)phenylacetic acid from Step 2 of Example 8 using the procedure given in Example 12. The crude product was purified by pressurized silica gel column chromatography using 3:2 EtOAc:hexanes as eluant. The free base was converted to the hydrochloride salt and the salt was lyophilized from acetonitrile:water to give the HCl salt of the title compound as an amorphous solid.

HPLC retention time=8.67 min (method A) TLC $R_f$=0.31 (3:2 EtOAc:hexanes); FAB MS: m/z=464 (M$^+$+H); combustion analysis: $C_{24}H_{28}F_3N_3O_3$, 0.45 HCl, 0.55 $H_2O$; Calculated C, 58.85; H, 6.08; N, 8.58; Found C, 58.85; H, 6.09; N, 8.32

EXAMPLE 33

1-(4-(4-piperidinyloxy)-2-(trifluoromethoxy) phenylacetyl)-2-carbamoyl-4-(2-methylphenyl) piperazine

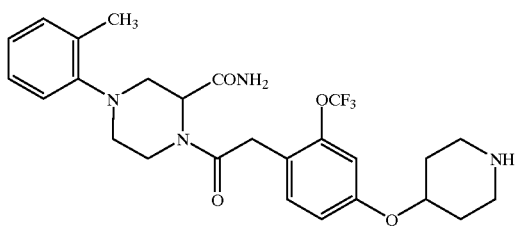

Step 1. To a stirred solution of 4-bromo-2-(trifluoromethoxy)iodobenzene (9.93 g, 28 mmol) in THF (150 mL) at −78° C. was added tert-butyllithium (37 mL of a 1.5 M solution in pentane, 56 mmol) dropwise over a period of 20 min. The pale yellow solution was stirred at −78° C. for 1.5 h when N-formylmorpholine (6.5 mL; 58 mmol) was added. The resulting solution was stirred at −78° C. for 15 min and the cooling bath was removed. The mixture was stirred for an additional 1 h, when 0.25 M aqueous citric acid (100 mL) was added. The mixture was diluted with EtOAc (150 mL), the layers were separated, the organic phase was washed with brine (100 mL), dried (MgSO$_4$), filtered, and the solvent was removed under reduced pressure. The residue was purified using pressurized silica gel column chromatography eluting with hexane to give 4-bromo-2-(trifluoromethoxy)benzaldehyde as a colorless liquid (TLC $R_f$=0.45 (hexanes)).

Step 2. To a stirred solution of 4-bromo-2-(trifluoromethoxy)benzaldehyde (5.0 g, 19 mmol) from Step 1 above in EtOH (100 mL) at 0° C. was added NaBH$_4$ (0.88 g, 23 mmol). The mixture was stirred for 1 h at 0° C., the cooling bath was removed, and the solution was stirred at ambient temperature for 14 h. The solvent was removed under reduced pressure and the residue was partitioned between EtOAc (150 mL) and saturated aqueous NaHCO$_3$ (75 mL). The organic phase was separated, dried (MgSO$_4$), filtered, and the solvent was removed under reduced pressure. The residue was purified by pressurized silica gel column chromatography using a gradient elution of 5–10% EtOAc:hexanes. 4-Bromo-2-(trifluoromethoxy)benzyl alcohol was obtained as an amorphous solid by evaporation from CH$_2$Cl$_2$ (TLC $R_f$=0.25 (10% EtOAc:hexanes); HPLC retention time=8.8 min (method A)).

Step 3. To a stirred solution of bromo-2-(trifluoromethoxy)benzyl alcohol (4.8 g, 18 mmol) in CH$_2$Cl$_2$ (100 mL) was added tert-butylchlorodimethylsilane (4.1 g, 27 mmol), triethylamine (3.8 mL, 27 mmol), and DMAP (1.2 g, 9.8 mmol). The mixture was stirred at ambient temperature for 24 h. The solvent was removed under reduced pressure and the residue was partitioned between EtOAc (150 mL) and 0.25 M aqueous citric acid (75 mL). The organic phase was washed with H$_2$O (50 mL), saturated aqueous NaHCO$_3$ (75 mL), dried (MgSO$_4$), filtered, and the solvent was removed under reduced pressure. The residue was purified by pressurized silica gel column chromatography using hexanes as eluant to give 4-bromo-1-(tert-butyldimethylsilyloxymethyl)-2-trifluoromethoxy-benzene as a colorless oil (TLC $R_f$=0.60 (hexanes)).

Step 4. To a stirred solution of 4-bromo-1-(tert-butyldimethylsilyloxymethyl)-2-trifluoromethoxybenzene (5.5 g, 15 mmol) from Step 3 above in THF (100 mL) at −78° C. was added n-butyllithium (6.6 mL of a 2.5 M solution in hexanes, 16.5 mmol) dropwise over a period of 10 min. The resulting pale yellow solution was stirred at −78° C. for 30 min and trimethylborate (1.75 g, 17 mmol) was added. The resulting solution was stirred at −78° C. for 5 min and then warmed to ambient temperature for 45 min. To the mixture was added acetic acid (0.90 mL, 15 mmol) and hydrogen peroxide (0.1.7 mL of a 30% solution in water, 17 mmol) and stirring was continued for 1 h. The solvent was removed under reduced pressure and the residue was partitioned between EtOAc (150 mL) and water (2×50 mL). The organic layer was dried (MgSO$_4$), filtered, and the solvent was removed under reduced pressure. The residue was purified by pressurized silica gel column chromatography using 10% EtOAc:hexanes as eluant to give 4-hydroxy-1-(tert-butyldimethyl-silyloxymethyl)-2-trifluoromethoxybenzene as a colorless oil (TLC $R_f$=0.40 (10% EtOAc:hexanes)).

Step 5. To a stirred solution of 4-hydroxy-1-(tert-butyldimethylsilyloxymethyl)-2-trifluoromethoxybenzene (3.2 g, 10 mmol) from Step 4 above and triphenylphosphine (3.9 g, 15 mmol) in THF (50 mL) at 0° C. was added a solution of N-tert-butyloxycarbonyl-4-piperidinol (3.0 g, 15 mmol) and DEAD (2.6 g, 15 mmol) in THF (25 mL) dropwise over a period of 1 h. The mixture was stirred at 0° C. for 3h and then at ambient temperature for 12 h. The solvent was removed under reduced pressure and the residue was suspended in ether. The solid triphenylphosphine oxide was removed by filtration and the filtrate was purified by pressurized silica gel column chromatography using a gradient elution of 5–10% EtOAc:hexanes as eluant to give 4-(N-tert-butyloxycarbonyl-4-piperidinyloxy)-1-(tert-butyldimethylsilyloxy-methyl)-2-trifluoromethoxybenzene as a colorless gum.

Step 6. To a stirred solution of 4-(N-tert-butyloxycarbonyl-4-piperidinyloxy)-1-(tert-butyldimethylsilyloxymethyl)-2-trifluoromethoxybenzene (3.5 g, 7.1 mmol) from Step 5 above in THF (50 mL) was added TBAF (8 mL of a 1.0 M solution in THF, 8 mmol). The mixture was stirred at ambient temperature for 5 minutes and the solvent was removed under reduced pressure. The residue was partitioned between EtOAc (100 mL) and water (2×50 mL). The organic phase was dried (MgSO$_4$), filtered, and the solvent was removed under reduced pressure. The residue was purified by pressurized silica gel column chromatography using a gradient elution of 25–50% EtOac:hexanes to give 4-(N-tert-butyloxycarbonyl-4-piperidinyloxy)-2-(trifluoromethoxy)benzyl alcohol as a colorless gum (TLC $R_f$=0.24 (25% EtOAc EtOAc:hexanes)).

Step 7. To a stirred solution of 4-(N-tert-butyloxycarbonyl-4-piperidinyloxy)-2-(trifluoromethoxy)benzyl alcohol (2.5 g, 6.6 mmol)) from Step 6 above and triphenylphosphine (3.46 g, 13.2 mmol) in ether (100 mL) was added carbon tetrabromide (4.35 g, 13 mmol). The mixture was stirred at ambient temperature for 14 h and the ethereal solution was decanted away from the gummy precipitate of triphenylphosphine oxide which had formed. The solvent was removed under reduced pressure and the residue was purified by pressurized silica gel column chromatography using a gradient elution of 10–15% EtOAc:hexanes to give 4-(N-tert-butyloxycarbonyl-4-piperidinyloxy)-2-(trifluoromethoxy)benzyl bromide as a colorless oil (TLC $R_f$=0.55 (25% EtOAc:hexanes)).

Step 8. To a stirred solution of 4-(N-tert-butyloxycarbonyl-4-piperidinyloxy)-2-(trifluoromethoxy)benzyl bromide (2.2 g, 5.0 mmol) in DMF (50 mL) was added NaCN (2.7 g, 5.5 mmol). The mixture was stirred at ambient temperature for 36 h. The solvent was removed under reduced pressure and the residue was purified by pressurized silica gel column chromatography using 25% EtOAc:hexanes as eluant to give 4-(N-tert-butyloxycarbonyl-4-piperidinyloxy)-2-(trifluoromethoxy)phenylacetonitrile as a colorless oil (TLC $R_f$=0.43 (25% EtOAc:hexanes); HPLC retention time=11.3 min (method A)).

Step 9. 4-(N-tert-butyloxycarbonyl-4-piperidinyloxy)-2-(trifluoromethoxy)phenylacetonitrile (1.9 g, 4.3 mmol) from Step 8 above dissolved in a 2:1 mixture of acetic acid and concentrated aqueous HCl (25 mL). Loss of the Boc group occurred within the first 5 minutes to give an intermediate which had an HPLC retention time of 6.3 min (method A). The solution was then refluxed for 2 h, during which time the 6.3 min peak disappeared and a new peak at 5.9 min appeared. The solvents were removed under reduced pressure. The residue was dissolved in degassed DMF (100 mL) and the solvent was removed under reduced pressure to minimize the amount of residual acetic acid and water in the sample. The crude product, 4-(4-piperidinyloxy)-2-(trifluoromethoxy)phenylacetic acid, was dissolved in DMF (50 mL) and di-tert-butyldicarbonate (1.0 g, 4.6 mmol) and DIEA (2.3 mL, 13 mmol) were added. The solution was stirred at ambient temperature for 30 min. The solvent was removed under reduced pressure and the residue was partitioned between EtOAc (100 mL) and 0.25 M aqueous citric acid (50 mL). The organic phase was separated, washed with water (2×25 mL), dried (MgSO$_4$), filtered, and the solvent was removed under reduced pressure to give 4-(N-tert-butyloxycarbonyl-4-piperidinyloxy)- 2-(trifluoromethoxy)phenylacetic acid as a gum (HPLC retention time=10.2 min (method A)).

Step 10. To a stirred solution of 4-(N-tert-butyloxycarbonyl-4-piperidinyloxy)-2-(trifluoromethoxy)phenylacetic acid (0.50 g, 1.15 mmol) from Step 9 above and 2-carbamoyl-4-(2-methyl-phenyl)piperazine (0.28 g, 1.1 mmol) from Step 4 of Example 1 in DMF (20 mL) was added HOBT (0.175 g, 1.15 mmol), EDC (0.53 g, 1.8 mmol), and DIEA (0.26 mL, 1.5 mmol). The solution was stirred at ambient temperature for 14 h and the solvent was removed under reduced pressure. The residue was partitioned between EtOAc (100 mL) and 0.25 M aqueous citric acid (75 mL). The organic phase was separated and washed with H$_2$O (25 mL), saturated aqueous NaHCO$_3$ (75 mL), and brine (25 mL). The organic phase was dried (MgSO$_4$), filtered, and the solvent was removed under reduced pressure. The residue was purified by pressurized silica gel column chromatography using EtOAc as eluant. The product-containing fractions were evaporated under reduced pressure to give 1-(1-(2-trifluoromethoxy-4-(N-tert-butyoxycarbonyl-4-piperidinyloxy)phenylacetyl)-2-carbamoyl-4-(2-methylphenyl)piperazine as an amorphous solid (HPLC retention time=11 min (method A); TLC $R_f$=0.5 (7:3 EtOAc:hexanes).

Step 11. Into a stirred solution of 1-(1-(2-trifluoromethoxy-4-(N-tert-butyoxycarbonyl-4-piperidinyloxy)phenylacetyl)-2-carbamoyl-4 -(2-methylphenyl)piperazine (0.65 g, 1.0 mmol) from Step 10 above in EtOAc (75 mL) at 0° C. was bubbled HCl gas for 15 min. The resulting suspension was stirred at 0° C. for 45 min. Excess HCl was removed by bubbling argon though the mixture for 15 min. Ether (75 mL) was added and the cold suspension was filtered. The solids were washed with additional ether and dried under reduced pressure for 18 h to give the hydrochloride salt of the title compound as an amorphous white powder.

HPLC retention time=7.48 min (method A) TLC $R_f$=0.42 (90:10:0.5 CH$_2$Cl$_2$:MeOH:NH$_4$OH); FAB MS: m/z=521 (M$^+$+H), 2.0 HCl, 0.62 H$_2$O; combustion analysis: C$_{26}$H$_{31}$F$_3$N$_4$O$_4$, 2.0 HCl, 0.62 H$_2$O; Calculated C, 51.65; H, 5.71; N, 9.27; Found C, 51.64; H, 5.62; N, 9.21

EXAMPLE 34

1-(4-(N-acetyl-4-piperidinyloxy)-2-(trifluoromethoxy)phenylacetyl)-2-carbamoyl-4-(2-methylphenyl)piperazine

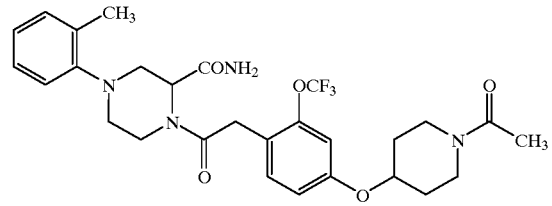

To a solution of 1-(4-(4-piperidinyloxy)-2-(trifluoromethoxy)phenylacetyl)-2-carbamoyl-4-(2-methylphenyl)piperazine hydrochloride (0.30 g, 0.5 mmol) from Example 33 in CH$_2$Cl$_2$ (50 mL) was added acetic anhydride (0.10 mL, 1.0 mmol) and DIEA (0.17 mL, 1.0 mmol). The solution was stirred at ambient temperature for 1 h and the solvent was removed under reduced pressure. The residue was dissolved in EtOAc (100 mL) and washed with 0.25 M aqueous citric acid (50 mL), H$_2$O (25 mL), and saturated aqueous NaHCO$_3$ (75 mL). The organic phase was dried (MgSO$_4$), filtered, and the solvent was removed under reduced pressure to give the title compound as an amorphous solid.

HPLC retention time=8.8 min (method A) TLC $R_f$=0.40 (95:5 CH$_2$Cl$_2$:MeOH); FAB MS: m/z=566(M$^+$+H); combustion analysis: C$_{28}$H$_{33}$F$_3$N$_4$O; Calculated C, 59.46; H, 5.88; N, 9.91; Found C, 59.47; H, 5.46; N, 9.95

EXAMPLE 35

1-(2-(2,2,2-trifluoroethoxy)phenylacetyl)-4-(3-ethylphenyl)piperazine

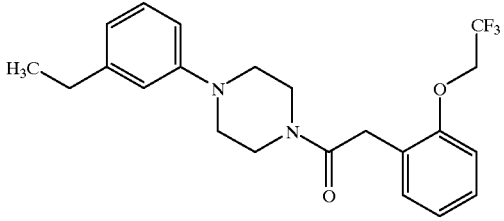

Step 1. Into a 15 mL round-bottomed flask fitted with a reflux condensor, a magnetic stirring bar, and a nitrogen inlet was added 1 mL dry toluene followed by 0.016 g (0.09 mmol) PdCl$_2$ and 0.055 g (0.18 mmol) tri-o-tolylphosphine. After stirring for 15 min, an additional 15 mL dry toluene was added followed by 0.33 g (1.8 mmol) 3-ethylbromobenzene, 0.41 g (2.2 mmol) 1-Boc-piperazine and 0.242 g (2.5 mmol) sodium t-butoxide. The reaction was heated to reflux for 18 hr, after which time TLC (20% EtOAc/Hexane) showed the formation of a new spot. The reaction was cooled, diluted with 50 mL of ether, filtered through a Celite pad, and extracted with 3×10 mL water and 1×15 mL brine. The organic phase was dried (Na2SO$_4$), filtered and the solvent removed in vacuo to get the crude product, which was purified by passing through a 2" silica pad (1% to 4% EtOAc/Hexane) to yield 1-Boc-4-(3-ethylphenyl)piperazine.

Step 2. 0.037 g (0.128 mmol) 1-Boc-4-(3-ethylphenyl)-piperazine from the previous step was dissolved in 10 mL EtOAc and cooled to 0° C. using an ice bath. HCl gas was then bubbled through the reaction for 10 min, followed by an additional 10 min of stirring. The reaction was warmed to ambient temperature and the solvent removed in vacuo. The residue was taken up in 10 mL CHCl$_3$ that had been previously saturated with NH$_3$ gas, the solid NH$_4$Cl filtered, and the solvent removed to give 1-(3-ethylphenyl)piperazine as the free base.

Step 3. 1-(3-ethylphenyl)piperazine from the previous step was dissolved in 1 mL dry DMF, and to the solution was added 0.03 g (0.128 mmol) 2-(2,2,2-trifluoroethoxy) phenylacetic acid, 0.017 g (0.128 mmol) HOBT, and 0.024 g (0.128 mmol) EDC. The reaction was stirred for 2 days, after which time the solvent was removed in vacuo and the resulting residue partitioned between EtOAc/H$_2$O. The aqueous phase was extracted with EtOAc and the combined organic phases were washed with H$_2$O, brine, dried over Na2SO$_4$ and filtered. Removal of the solvent and subsequent purification via preparative TLC (2:1 Hexane/EtOAc) yielded the title compound as the free base. This was dissolved in 20 mL EtOAc and an excess of ethanolic HCl was added. The solvent was removed to give the Hcl salt of the title compound.

HPLC retention time=11.2 min (method D) TLC R$_f$=0.37 (1:1 EtOAc:hexanes); FAB MS: m/z=407 (M$^+$+H); combustion analysis: C$_{22}$H$_{25}$F$_3$N$_2$O$_2$, 1.0 HCl, 0.25 ether; Calculated C, 59.86; H, 6.23; N, 6.07; Found C, 60.25; H, 5.95; N, 6.11

EXAMPLE 36

As a specific embodiment of an oral composition, 100 mg of the compound of Example 1 is formulated with sufficient finely divided lactose to provide a total amount of 580 to 590 mg to fill a size O hard gel capsule.

Also as an embodiment of the instant invention is a use of the compounds disclosed herein for preparing a medicament for the purpose of treating/preventing the clinical conditions for which an oxytocin receptor antagonist is indicated.

EXAMPLE 37

Rat & Human ot/avp Binding Assays

The high affinity binding of [$^3$H]oxytocin (OT) to uterine tissue and [$^3$H]arginine vasopressin (AVP) to liver (AVP-V$_1$ site) and kidney (AVP-V$_2$ site) tissue was determined using crude membrane preparations as described previously [Pettibone, D. J., et al., *J. Pharmacol. and Exper. Ther.*, 256(1): 304–308 (1991)]. Uterine tissue was taken from nonpregnant adult Sprague-Dawley rats (Taconic Farms, Germantown, N.Y.) pretreated (18–24 h) with diethylstilbestrol propionate (DES; 300 μg/kg, i.p.). Uterine tissue (full thickness) was also taken with informed consent from nonlabor pregnant women undergoing cesarean section at 38 to 39 weeks gestation (Oregon Health Sciences Center, Portland, Or.). Liver and kidney medulla samples were taken from male rats and from human surgical and early postmortem donors (National Disease Research Interchange, Philadelphia Pa.; Analytical Biological Services, Wilmington, De.).

Competition studies were conducted at equilibrium using 1 nM [$^3$H]OT or 0.5 nM [$^3$H]AVP in the following buffer: 50 mM Tris, 5 mM MgCl$_2$, 0.1% bovine serum albumin. Nonspecific binding was determined using 1 μM unlabeled OT or AVP in their respective assays. The binding reactions were initiated by the addition of tissue preparation and terminated by filtration using a Skatron cell harvester (model 7019, Skatron, Inc., Sterling, Va.). Ki values were calculated for each compound using three to six separate IC$_{50}$ determinations (Ki=IC$_{50}$/[1-c/K$_d$]); [Cheng, Y-C; Prusoff, W. H.; *Biochem. Pharmacol.* 22:3099 (1973)] with mean K$_d$ values obtained from replicate (n=3) equilibrium saturation binding assays (10 point, 100 fold concentration range): [$^3$H]OT rat uterus, 0.69 nM; human myometrium, 1.1 nM; [$^3$H]AVP: rat liver, 0.21 nM; rat kidney, 0.27 nM; human liver, 0.27 nM; human kidney, 1.4 nM. Computer analysis of the saturation assays by EBDA/LIGAND [McPherson, G. A.: Kinetic, Ebda, Ligand, Lowry: A Collection of Radioligand Binding Analysis Programs, Elsevier Science Publishers, Amsterdam (1985)] indicated that both radioligands apparently bound to single sites in all tissues examined. The final protein concentration for the various tissues in each assay ranged from 150 to 300 μg/ml [Lowry, P. H.; Rosebrough, N. J.; Farr, A. L.; Randall, R. J.; *J. Biol. Chem.*, 193:265–275 (1951)].

IC$_{50}$ values were determined for the [$^3$H]OT and [$^3$H]AVP binding assays by linear regression of the relation log concentration of compound vs. percent inhibition of specific binding. Data is either reported as a given percentage of inhibition at a specified concentration, or if an IC$_{50}$ was calculated, as a nanomolar concentration. Representative compounds of the present invention were found to have IC$_{50}$ values for oxytocin in the range of 1–500 nM.

The oxytocin antagonistic effect of the compounds of the present invention can be further evaluated according to the in vitro and/or in vitro functional assays described in detail in D. J. Pettibone et al., *Drug Devel. Res.* 1993, 30, 129–142.

While the foregoing specification teaches the principles of the present invention, with examples for the purpose of illustration, it will be understood that the practice of the invention encompasses all of the usual variations, adaptions and/or modifications as come within the scope of the following claims and their equivalents.

What is claimed is:

1. A compound of the formula I

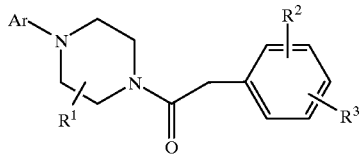

(I)

or a pharmaceutically acceptable salt thereof
wherein:
Ar is unsubstituted, mono-, or disubstituted phenyl, naphthyl, pyridyl, pyrazinyl, or pyrimidyl, in which the substituents on carbon are independently selected from the group consisting of: $C_{1-5}$ alkyl, $C_{1-5}$ alkoxyl, halogen, nitro, cyano, and $CF_3$;
$R^1$ is $CON(R^4)_2$;
$R^2$ is $OCH_2CF_3$;
$R^3$ is

$R^4$ is independently selected from the group consisting of hydrogen and $C_{1-5}$ alkyl; and
$R^7$ is selected from the group consisting of hydrogen, $C_{3-7}$ cycloalkyl substituted $C_{1-5}$ alkyl, $SO_2$-$C_{1-5}$ alkyl, $CO$-$C_{1-5}$ alkyl, and hydroxy $C_{1-5}$ alkyl.

2. A compound of claim 1 wherein
Ar is mono-$C_{1-5}$ alkylsubstituted phenyl;
$R^1$ is $CONH_2$;
$R^2$ is $OCH_2CF_3$; and
R3 is

3. A compound of claim 2 of the Structure II:

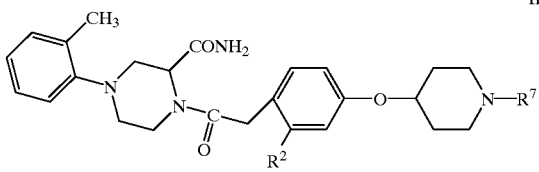

II or pharmaceutically acceptable salts thereof.

4. A compound of claim 1 selected from the group consisting of:

1-(4-(4-piperidinyloxy)-2-(2,2,2-trifluoroethoxy) phenylacetyl)-2-carbamoyl-4-(2-methylphenyl) piperazine;

1-(4-(N-cyclopropylmethyl-4-piperidinyloxy)-2-(2,2,2,-trifluoroethoxy)phenylacetyl)-2-carbamoyl-4-(2-methylphenyl)piperazine;

1-(4-(N-methylsulfonyl-4-piperidinyloxy)-2-(2,2,2-trifluoroethoxy)-phenylacetyl)-2-carbamoyl-4-(2-methylphenyl)piperazine;

1-(4-(N-acetyl-4-piperidinyloxy)-2-(2,2,2-trifluoroethoxy)phenyl-acetyl)-2-carbamoyl-4-(2-methylphenyl)piperazine;

1-(4-(N-2-methyl-2-hydroxypropyl-4-piperidinyloxy)-2-(2,2,2-trifluoroethoxy)phenylacetyl)-2-carbamoyl-4-(2-methylphenyl)-piperazine;

or pharmaceutically acceptable salts thereof.

5. A pharmaceutical composition comprising the compound of claim 1 and a pharmaceutically acceptable carrier.

6. A method of eliciting an oxytocin antagonizing effect in a mammal in need thereof, comprising administering to the mammal a therapeutically effective amount of the compound of claim 1.

7. A method of treating preterm labor in a mammal in need thereof, comprising administering to the mammal a therapeutically effective amount of the compound of claim 1.

8. A method of stopping labor preparatory to caesarian delivery in a mammal in need thereof, comprising administering to the mammal a therapeutically effective amount of the compound of claim 1.

9. A method of treating dysmenorrhea in a mammal in need thereof, comprising administering to the mammal a therapeutically effective amount of the compound of claim 1.

10. A method of increasing fertility and embryonic survival in a farm animal, comprising administering to the farm animal a therapeutically effective amount of the compound of claim 1.

11. A method for improving survival of a farm animal neonate comprising controlling timing of parturition to effect delivery of the neonate during daylight hours by administering to a farm animal which is expected to deliver the neonate within 24 hours a therapeutically effective amount of the compound of claim 1.

12. A method of controlling the timing of estrus in a farm animal, comprising administering to the farm animal a therapeutically effective amount of the compound of claim 1.

* * * * *